US011860082B1

United States Patent
Bellemare et al.

(10) Patent No.: US 11,860,082 B1
(45) Date of Patent: Jan. 2, 2024

(54) METHOD OF DETERMINING AN INDEX OF QUALITY OF A WELD IN A FORMED OBJECT THROUGH MECHANICAL CONTACT TESTING

(71) Applicant: Massachusetts Materials Technologies LLC, Natick, MA (US)

(72) Inventors: Simon C. Bellemare, Weston, MA (US); Steven D. Palkovic, Somerville, MA (US); Brendon M. Willey, Dedham, MA (US); Soheil Safari Loaliyan, Everett, MA (US); Parth P. Patel, Brighton, MA (US)

(73) Assignee: Massachusetts Materials Technologies LLC, Natick, MA (US)

( * ) Notice: Subject to any disclaimer, the term of this patent is extended or adjusted under 35 U.S.C. 154(b) by 1027 days.

(21) Appl. No.: 16/515,817

(22) Filed: Jul. 18, 2019

Related U.S. Application Data

(60) Provisional application No. 62/699,980, filed on Jul. 18, 2018.

(51) Int. Cl.
| | |
|---|---|
| *G01N 19/08* | (2006.01) |
| *G01N 33/207* | (2019.01) |
| *G01B 11/02* | (2006.01) |

(Continued)

(52) U.S. Cl.
CPC ............. *G01N 19/08* (2013.01); *G01B 11/02* (2013.01); *G01N 1/32* (2013.01); *G01N 3/42* (2013.01);

(Continued)

(58) Field of Classification Search
CPC ........ G01N 19/08; G01N 33/207; G01N 1/32; G01B 11/02

(Continued)

(56) References Cited

U.S. PATENT DOCUMENTS

| | | | | |
|---|---|---|---|---|
| 4,820,051 A | * | 4/1989 | Yanagisawa | ............. G01N 3/42 |
| | | | | 356/626 |
| 6,945,097 B2 | * | 9/2005 | Jardret | ..................... G01N 3/46 |
| | | | | 73/806 |

(Continued)

FOREIGN PATENT DOCUMENTS

| | | | | |
|---|---|---|---|---|
| CN | 1674850 A1 | * | 6/2006 | |
| EP | 3267176 A1 | * | 1/2018 | ............... G01N 3/46 |

(Continued)

OTHER PUBLICATIONS

Translation WO-2012101371 (Year: 2012).*

*Primary Examiner* — Alexander A Mercado
*Assistant Examiner* — Monica S Young
(74) *Attorney, Agent, or Firm* — Sunstein LLP

(57) ABSTRACT

A method for evaluating a weld in a formed object includes performing a contact mechanics test of a first region that includes the weld and storing one or more corresponding weld surface mechanical property measurements, performing a contact mechanics test of a second region that excludes the weld and storing one or more corresponding base material surface mechanical property measurements, determining a relative difference in the weld surface mechanical property measurements and the base material surface mechanical property measurements, determining one or more weld width measurements on the exterior surface of the formed object, and evaluating the weld based on the determined relative difference in the weld surface mechanical property measurements and the base material surface mechanical property measurements in relation to the determined weld width measurements in order to provide an index of weld quality that is traditionally measured through a destructive test or examination.

20 Claims, 28 Drawing Sheets

(51) Int. Cl.
*G01N 1/32* (2006.01)
*G01N 3/42* (2006.01)
*G01N 3/46* (2006.01)

(52) U.S. Cl.
CPC ............. *G01N 3/46* (2013.01); *G01N 33/207* (2019.01); *G01N 2203/0082* (2013.01)

(58) Field of Classification Search
USPC .............................................................. 73/9
See application file for complete search history.

(56) References Cited

U.S. PATENT DOCUMENTS

| | | | | |
|---|---|---|---|---|
| 9,513,200 | B1* | 12/2016 | Dubke | G01N 3/20 |
| 9,863,891 | B1* | 1/2018 | Lara Magallanes | G01N 21/952 |
| 9,921,128 | B2* | 3/2018 | Yang | G01N 3/42 |
| 2002/0105325 | A1* | 8/2002 | Goldfine | G01N 27/82 324/242 |
| 2004/0128016 | A1* | 7/2004 | Stewart | G05B 19/4099 700/159 |
| 2008/0028840 | A1* | 2/2008 | Smith | G01N 3/42 73/78 |
| 2009/0260427 | A1* | 10/2009 | Woirgard | G01Q 60/366 73/85 |
| 2010/0281963 | A1* | 11/2010 | Greer | G01Q 60/366 73/82 |
| 2014/0373608 | A1* | 12/2014 | Bellemare | G01N 3/46 73/82 |
| 2016/0084802 | A1* | 3/2016 | Yusuf | G01N 29/4436 73/582 |
| 2016/0258852 | A1* | 9/2016 | Bellemare | G06F 30/23 |
| 2016/0282246 | A1* | 9/2016 | Yang | G01N 3/42 |
| 2016/0370272 | A1* | 12/2016 | Bellemare | G01N 3/60 |
| 2017/0312862 | A1* | 11/2017 | Wasson | B23K 35/0288 |
| 2020/0130089 | A1* | 4/2020 | Ivkovich | B23K 9/0953 |

FOREIGN PATENT DOCUMENTS

| | | | | | |
|---|---|---|---|---|---|
| JP | 2004053427 | A | * | 2/2004 | |
| JP | 2006219717 | A | * | 8/2006 | |
| WO | WO-2012101371 | A1 | * | 8/2012 | G06Q 10/06 |
| WO | WO-2014205402 | A1 | * | 12/2014 | G01N 3/46 |

* cited by examiner $L_{HAZ}/t = 121\% \pm 28\%$
(10 samples)

$L_{HAZ}/t = 46\% \pm 8\%$
(7 samples)

$L_{HAZ}/t = 253\% \pm 56\%$
(15 samples)

METHOD OF DETERMINING AN INDEX OF QUALITY OF A WELD IN A FORMED OBJECT THROUGH MECHANICAL CONTACT TESTING

CROSS REFERENCE TO RELATED APPLICATIONS

The present application claims priority to U.S. Provisional Patent Application No. 62/699,980 filed Jul. 18, 2018, the disclosure of which is incorporated by reference herein in its entirety.

TECHNICAL FIELD

The present invention relates to the evaluation of a weld in a formed object through the determination of relative differences in surface mechanical properties measured in a region containing the weld and a region excluding the weld, and the determination of a width of the weld. Additional parameters may be combined with these determinations to provide a more accurate or reliable evaluation of the weld.

BACKGROUND ART

Many engineering applications require the use of load bearing members which are fabricated by forming initially flat pieces of stock material into geometries that are suitable for the intended function. These formed objects commonly use welds to join opposing edges or faces to form a mechanical bond. One example is a welded pipe joint where a flat plate is rolled into a steel tube, and then a weld is fabricated along the length of the tube to create a closed cylinder that can withstand internal pressures. For safe operation, these welds should meet the performance of the initial formed objects so that they do not create regions that are susceptible to failures under service loadings. Knowledge of the weld properties is even more critical for older infrastructure, which was built with outdated manufacturing methods, required less rigorous quality specifications, and for which material test data from the time of construction may no longer be available.

The evaluation of the weld mechanical integrity and durability has traditionally required the removal of a section of the formed object containing the weld for a laboratory evaluation using standardized techniques. These laboratory techniques allow for the measurement of stiffness, strength, ductility, resistance to crack propagation, and resistance to cyclic loading. The data collected from these methods can be used to determine the capacity, risk, and remaining life of a formed object with a weld. Another important consideration for evaluating the quality of the weld is to determine the welding process used during fabrication. The quality, reliability and durability of welds is known to vary between processes, and manufacturing capabilities have changed over time due to advances in construction methods. For pipelines, a welded pipe joint is typically fabricated with lap welding, electric-resistance-welding (ERW), flash-welding, or submerged-arc-welding (SAW), and each weld type has unique risks and benefits. ERW pipes can be further classified as a low frequency (LF-ERW) process that was used from 1920 to 1960, a high frequency (HF-ERW) process which almost completely replaced LF by 1970, and a high frequency normalized (HFN-ERW) process that has been subjected to an additional effective post-weld-heat-treatment (PWHT). Some pipeline operators will assign different weld properties to the pipe joint based on the evaluation of the weld process because of the known influence on weld performance. The current practice for classifying these different weld processes is to remove a sample of the pipe wall containing the weld and perform a metallographic analysis.

This existing approach to evaluating the quality of a weld is challenging for in-service assets where a section of the formed object cannot be easily removed for standardized examination and testing.

SUMMARY OF THE EMBODIMENTS

In accordance with one embodiment of the invention, a method of evaluating a weld in a formed object having an exterior surface includes (a) performing, on the exterior surface of the formed object, a contact mechanics test of a first region that includes the weld and storing one or more corresponding weld surface mechanical property measurements, (b) performing, on the exterior surface of the formed object, a contact mechanics test of a second region that excludes the weld and storing one or more corresponding base material surface mechanical property measurements, (c) determining a relative difference in the weld surface mechanical property measurements and the base material surface mechanical property measurements, (d) determining one or more weld width measurements on the exterior surface of the formed object, and (e) evaluating the weld based on the determined relative difference in the weld surface mechanical property measurements and the base material surface mechanical property measurements in relation to the determined weld width measurements to provide an index of weld quality.

In related embodiments, the contact mechanics test of the first region and the contact mechanics test of the second region may be performed using a single frictional sliding test or multiple frictional sliding tests. The contact mechanics test of the first region and/or the contact mechanics test of the second region may be performed using a grid or linear array of indentations. Determining the relative difference in the weld surface mechanical property measurements and the base material surface mechanical property measurement may include comparing an average of the weld surface mechanical property measurements and an average of the base material surface mechanical property measurements. Determining the relative difference in the weld surface mechanical property measurements and the base material surface mechanical property measurement may include examining local maxima and minima in the weld surface mechanical property measurements with respect to the base material surface mechanical property measurements. Determining the weld width measurement includes applying an etchant to the exterior surface of the weld to determine an etched weld width based on size of discolored material within the weld. Performing the contact mechanics test of the first region may include determining a first region weld surface mechanical property profile and/or performing the contact mechanics test of the second region may include determining a second region weld surface mechanical property profile, wherein determining the one or more weld width measurements includes analyzing relative changes in the first region weld surface mechanical property profile and/or in the second region weld surface mechanical property profile to determine a weld width. The index of weld quality may include a weld toughness, a maximum weld allowable flaw size, and/or a classification of a welding process. The evaluating step may include using one or more weld surface mechanical property measurements, base material surface mechanical property measurements, and/or weld width measurements stored in a weld database. In this case, the method may further include providing, to the database, the index of weld quality and parameters used in evaluating the index of weld quality. The evaluating step may further include determining a confidence interval of the index. The method may further include performing a chemical analysis to determine chemical composition of the formed object and/or the weld, wherein the index of weld quality is further based on the chemical composition. In this case, determining the chemical composition may include determining the carbon equivalent. The method may further include performing a weld microstructural analysis, wherein the index of weld quality is further based on the weld microstructural analysis. The method may further include determining an index of vintage of the formed object, wherein the index of weld quality is further based on the index of vintage. The method may further include determining a weld defect, wherein the index of weld quality is further based on the weld defect. The method may further include determining a base material bulk mechanical property, wherein the index of weld quality is further based on the base material bulk mechanical property. The method may further include (a) performing a chemical analysis to determine chemical composition of the formed object, (b) performing a chemical analysis to determine chemical composition of the weld, (c) performing a weld microstructural analysis, (d) determining an index of vintage of the formed object, (e) determining a weld defect, and/or (f) determining a base material bulk mechanical property, wherein the index of weld quality is based on two or more of the chemical composition of the formed object, the chemical composition of the weld, the weld microstructural analysis, the index of vintage, the base material bulk mechanical property, or the weld defect.

BRIEF DESCRIPTION OF THE DRAWINGS

The foregoing features of embodiments will be more readily understood by reference to the following detailed description, taken with reference to the accompanying drawings, in which:

FIGS. 4A and 4B show a perspective view and cross-sectional view, respectively, of an indentation test. FIGS. 4C and 4D show a perspective view and cross-sectional view, respectively, of a frictional sliding test. FIG. 4E shows a perspective view of another frictional sliding test using a wedge-shaped stylus with stretch passage. FIGS. 4F and 4G show perspective views of frictional sliding tests and indentation tests, respectively, performed in a circumferential direction.

FIG. 9A shows a perspective view of a formed object with a longitudinal weld and FIG. 9B shows a side view of a formed object with a fillet weld.

FIGS. 15A and 15B are cross-sectional views of a lack of fusion defect and cold weld defect, respectively. FIGS. 15C and 15D are perspective and cross-sectional views, respectively, of a stitching defect. FIGS. 15E-15G show cross-sectional views of cracks and pores, selective weld seam corrosion defect, and weld trim defect, respectively.

Figure 1A:
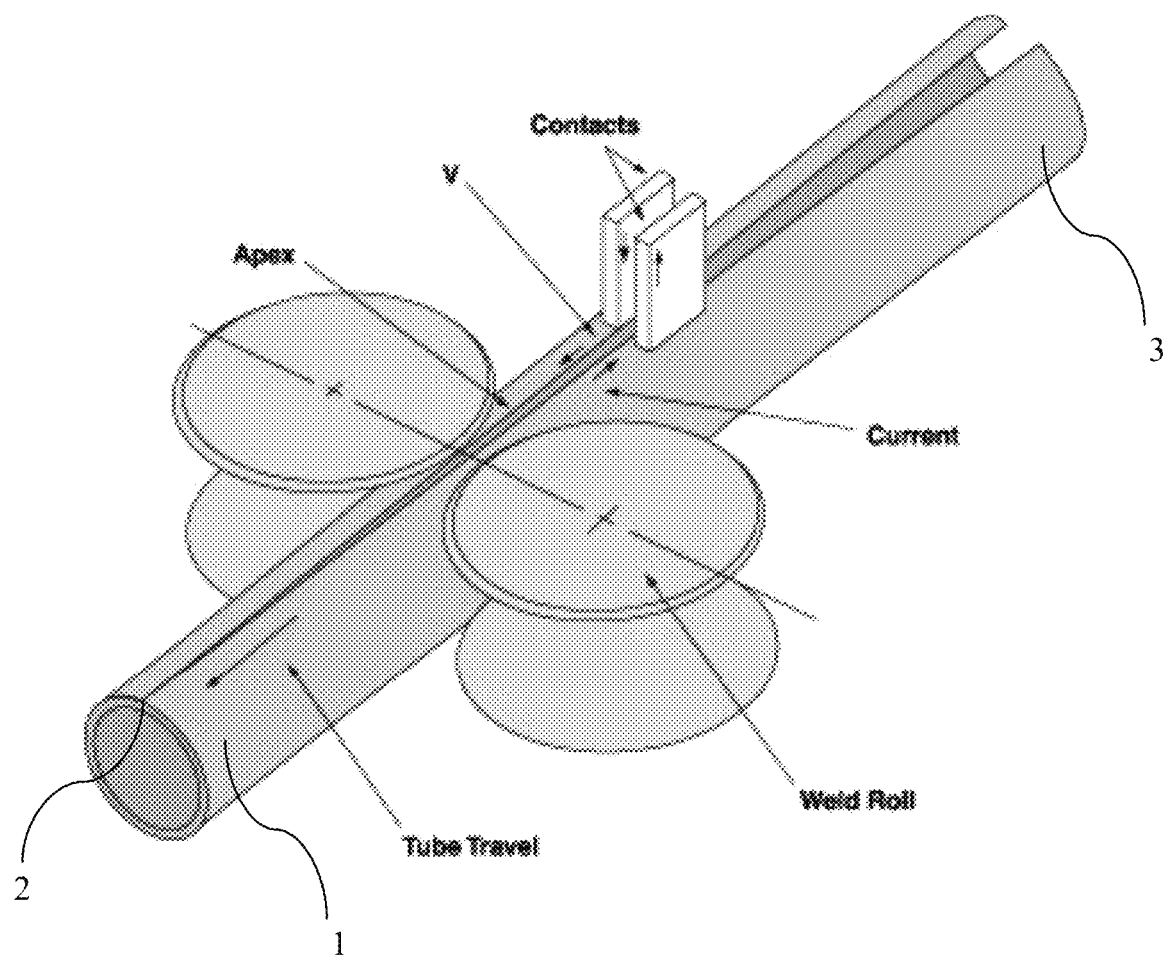
FIG. 1A shows a perspective view of a welding process on a formed object and FIGS. 1B-1E show cross-sectional views of different welds on formed objects.

19B is a graph showing an index of toughness versus Charpy V-Notch measurements for a weld toughness unity plot.

DETAILED DESCRIPTION OF SPECIFIC EMBODIMENTS

Definitions. As used in this description and the accompanying claims, the following terms shall have the meanings indicated, unless the context otherwise requires:

A "formed object" is a component that has been manufactured through bending, rolling, extrusion, and/or other fabrication processes. A formed object includes pipe joints, tubing, fittings, and other structural members. The material of the formed object may be metal, polymer, elastomer or composite.

A "weld" is a region where two opposing sides of a formed object have been mechanically joined through the application of heat and/or pressure. The weld includes material surrounding the joined edges including a "heat-affected-zone", which is a region of material that has experienced changes in mechanical properties, microstructure, chemistry, and/or internal stresses as a result of the joining process. The weld may consist of filler material that was added near the contacting sides of the formed object during the joining process.

A "base material" is a region of the formed object that is away from the weld and has not been affected by the joining process.

A "bondline" is the region of the weld where the opposing edges of a formed object meet. Not all welds have well-defined bondlines.

A "contact point" is a region where electrodes used during the welding process contact the outer surface of the formed object. The contact point may be outside of the weld, or it may intersect and overlap with the weld. The contact point may be intermittent spot locations or a line. Not all welds have contact points.

A "post-weld-heat-treatment" is a step in the manufacturing process for a formed object with a weld that is applied to normalize changes in the weld and surrounding material that were caused by the joining process. The results of a post-weld-heat-treatment will vary depending on processing conditions, geometry of the formed object, and the material properties of the formed object and weld. Not all welds are subjected to a post-weld-heat-treatment.

An "asymmetric heat-affected-zone" is a heat-affected-zone where a post-weld-heat-treatment was applied to the weld that was not centered on the bondline.

A "stylus" is an element that engages with a formed object to produce deformation on the surface.

A "substrate" is the material on the formed object that is deformed by a stylus.

A "contact mechanics test" is the use of localized deformation to probe the mechanical response of a material while the rest of the formed object remains unchanged. Specific implementations include an "indentation test" where a hard stylus deforms the surface of a softer substrate by moving perpendicular to the substrate surface. Another implementation is a "frictional sliding test" where a hard stylus is indented into the surface of a softer substrate and then slides laterally along the substrate surface.

A "stylus trajectory" is the physical path of a stylus with respect to the substrate that the stylus follows during a contact mechanics test. A stylus trajectory may consist of multiple indentations that are performed in a grid or linear array. A stylus trajectory may also consist of the direction and length of the groove or scratch that is created during a frictional sliding test.

A "surface mechanical property" is a measurement of the mechanical property of a substrate through a contact mechanics test. Examples of surface mechanical properties include a "hardness", which is a measure of the substrate resistance to plastic deformation that is applied by a spherical or blunted stylus. The hardness has units of force per unit area or load per unit area and is correlated to the material plastic properties. Another example of a surface mechanical property is a "fractured ligament height", which is a measure of the substrate resistance to local tensile separation that is applied by a wedge-shaped stylus with a stretch passage. The fractured ligament height has units of length and is correlated to the material crack-tip-opening-displacement.

A "weld surface mechanical property" is a surface mechanical property measurement collected in the weld of the formed object. Examples include a "weld hardness" and a "weld fractured ligament".

A "base material surface mechanical property" is a surface mechanical property measurement collected away from the weld in the base material of the formed object. Examples include a "base material hardness" and a "base material fractured ligament".

A "surface mechanical property profile" is a collection of surface mechanical property measurements that show relative changes along a stylus trajectory. Examples include a "hardness profile" and a "fractured ligament profile"

A "weld surface mechanical property profile" is a surface mechanical property profile that contains a weld. Examples include a "weld hardness profile" and a "weld fractured ligament profile".

A "weld width" is a measurement of the size of the weld that reflects the duration and magnitude of heat input during one or more fabrication steps. The width of the weld may be determined through the following:

i. an "etched weld width" is the size of the weld that is measured after the application of a corrosive solution, or "etchant", to a region on the surface of the formed object that includes the weld and some of the surrounding base material. This process results in the visual discoloration of weld material, while the surrounding base material is not visibly changed. Etching the weld and surrounding base material may also allow for visualization of the bondline and contact points.

ii. a "surface mechanical property width" is the size of the weld that is determined from a weld surface mechanical property profile. This may consist of material in-between base material regions on opposing sides of a weld. A "hardness weld width" is determined from a weld hardness profile, and the "fractured ligament width" is determined from a weld fractured ligament profile.

A "chemical composition" is the measurement of the weight percentage of chemical elements present in the material of the formed object and/or weld that is determined from chemical analysis.

An "index of vintage" is a determination of the year or time period that the formed object was manufactured which reflects the quality of processing controls and manufacturing technology at the time the formed object was constructed.

A "microstructure profile" is the determination of changes in a microstructure property at different regions in a formed object. This may include the changes in microstructure properties from the base material and through the weld to the bondline. A microstructure profile that contains the weld is a "weld microstructure profile".

A "grain" is a structure made of atoms sitting together with a specific formations and order in a three-dimensional space. The "grain size" is a microstructure property which is the measurement of the geometrical size of a grain in a microstructure.

A "microstructure phase" is a kinetically and thermodynamically stable or meta-stable formation of atoms and/or molecules in a solid that determines physical and mechanical properties of the solid. The volume fraction of a microstructure phase is an example of a microstructure property.

A "weld microstructure analysis" is the examination of a weld microstructure profile to quantify and examine changes in the microstructure properties through the weld.

A "weld defect" is a flaw or anomaly local to the weld that increases the risk of a failure in the weld and reduces the capacity.

A "defect measurement device" is an instrument used to locate, identify, and determine the size of weld defects An "index of weld quality" is an evaluation of the mechanical integrity and durability of a weld. The index of weld quality may be traditionally measured with a destructive test where material is extracted from the formed object and sent to a laboratory where it is examined and/or tested until failure. Examples include:
  iii. a "welding process" is the manufacturing method used to form the weld. Each weld process has different risks and performance specifications that relate to the quality of the weld. A welding process includes flash-welded, submerged-arc-welded (SAW), single SAW (SSAW), double SAW (DSAW) and electric-resistance-welded (ERW) welds. The weld process for ERW welds can be further classified as low frequency (LF-ERW), high frequency (HF-ERW), and high frequency normalized (HFN-ERW).
  iv. a "weld toughness" is a measurement of the energy required to propagate a crack in the weld. Weld toughness may be measured through Charpy V-Notch (CVN) testing, Izod impact testing, and/or quasi-static crack growth to measure the fracture toughness resistance curve using compact tension (CT), single-edge notched bend (SEB), or other suitable fracture toughness specimen.
  v. A "maximum weld allowable flaw size" is a determination of the maximum crack-like defect that can be tolerated by the weld. The maximum weld allowable flaw size can be compared to the actual defect sizes determined from a defect measurement device to verify the capacity and service life of a formed object with a weld.

A "base material bulk mechanical property" is a measurement of the strength, toughness, and/or ductility of the base material of the formed object. Bulk indicates that the measurement considers the geometry and wall thickness of the formed object and measures a much greater volume than the surface mechanical property measured with a contact mechanics test. The evaluation of an index of weld quality may be given with respect to the base material bulk mechanical property as a relative difference or proportion.

A "classification model" is a predictive relationship that correlates one or more measurements performed on a weld and formed object to one or more categories of an index of weld quality that share similar characteristics. This may consist of evaluating the category of welding process.

A "regression model" is a predictive relationship that correlates one or more measurements performed on a weld and formed object to an index of weld quality. This may consist of evaluating a weld toughness or maximum weld allowable flaw size.

A "weld database" is a collection of data obtained from formed objects with welds that are used to develop the predictive relationships and validate the performance of those predictive relationships of a classification model and/or regression model.

A "confidence interval" is a statistical metric of uncertainty in the prediction of an index of weld quality which can be evaluated based on the performance of a classification model and/or regression model on a weld database.

Overview of Method and Applications

Embodiments of the present invention provide a method of evaluating welds in formed objects using measurements provided by multiple nondestructive techniques, and then using specific relationships with respect to those measurements in a predictive model in order to provide an index of weld quality that is traditionally measured using destructive laboratory examination or testing. The present evaluation method is suitable for testing on in-situ or in-service components, which saves time and costs while increasing operational safety.

The method makes use of contact mechanics techniques that probe the mechanical properties of the surface material on the formed object and weld. For example, U.S. Pat. No. 9,897,523 entitled "Contact Mechanic Tests Using Stylus Alignment to Probe Material Properties" describes one contact mechanics testing technique used on curved surfaces with a portable apparatus, which is incorporated by reference herein in its entirety. Specifically, U.S. Pat. No. 9,897,523 describes the use of an alignment mechanism and engagement mechanism to perform a frictional sliding test. In addition, U.S. Patent Application Publication No. 2018/0275035 entitled, "Measurement of Material Properties under Local Tensile Stress through Contact Mechanics" describes another contact mechanics testing technique that uses a wedge-shaped stylus with a stretch passage that measures material fracture toughness, which is incorporated by reference herein in its entirety. Either or both of these contact mechanics tests may be used to provide the weld or base material surface mechanical property measurements according to embodiments of the present invention.

Referring to FIGS. 1A-1E, formed objects 1 include pipe joints, tubing, fittings, and structural members. Many of these formed objects contain a weld 2 which is a region where two opposing sides of a formed object 1 are mechanically joined. The quality of the weld 2 can be characterized in terms of its mechanical properties and durability over time and is a critical factor in assessing the reliability and risk of a formed object 1 for engineering applications. Traditionally, the weld 2 can only be evaluated by removing a section of the formed object 1 containing the weld 2 and sending it to a laboratory for a destructive assessment where it is prepared and tested in accordance with industry standards. The methods and embodiments in this invention provide a novel approach to evaluating welds 2 in a formed object 1 without the need for removing material for traditional destructive assessments. This allows for direct in-situ assessment of formed objects 1 with welds 2 without the need for a change in operation or a repair after the evaluation. The results of these assessments can be used to perform quality control of new manufacturing and condition assessment of the risk, capacity, and remaining life in existing assets. Applications of the invention include the evaluation of pipelines, structural connections, and built-up structural members.

Figure 1B:
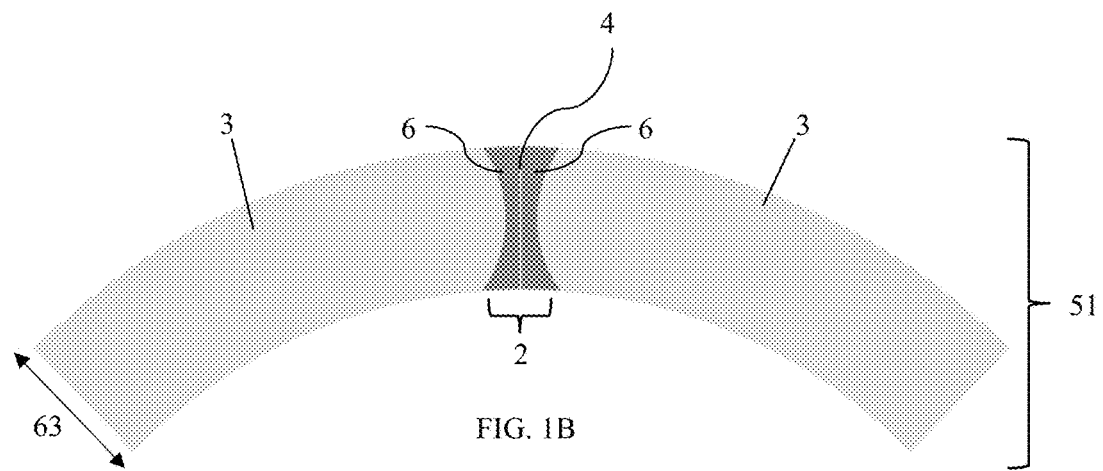
Figure 1C:
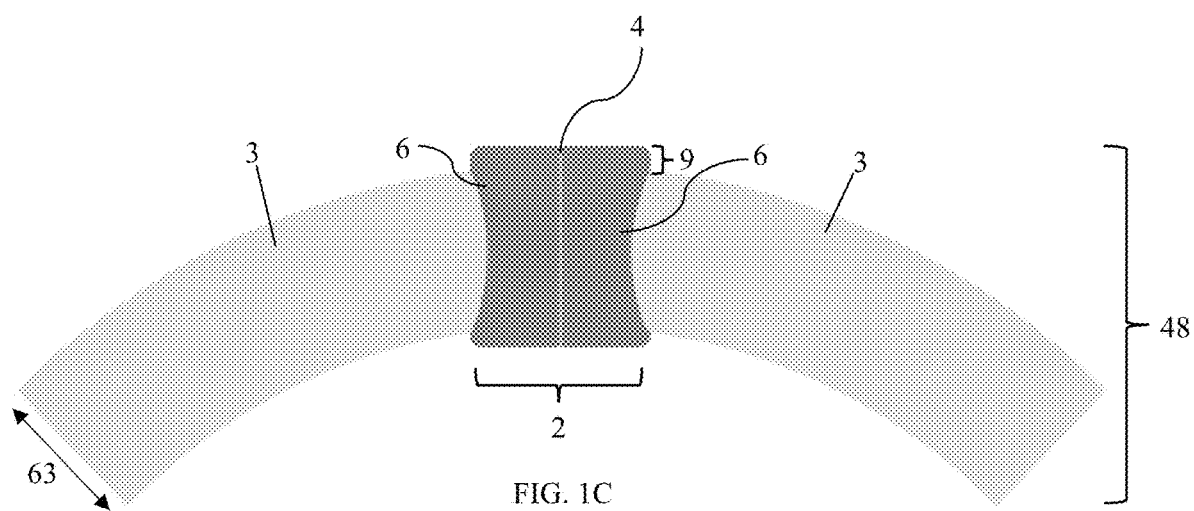
Figure 1D:
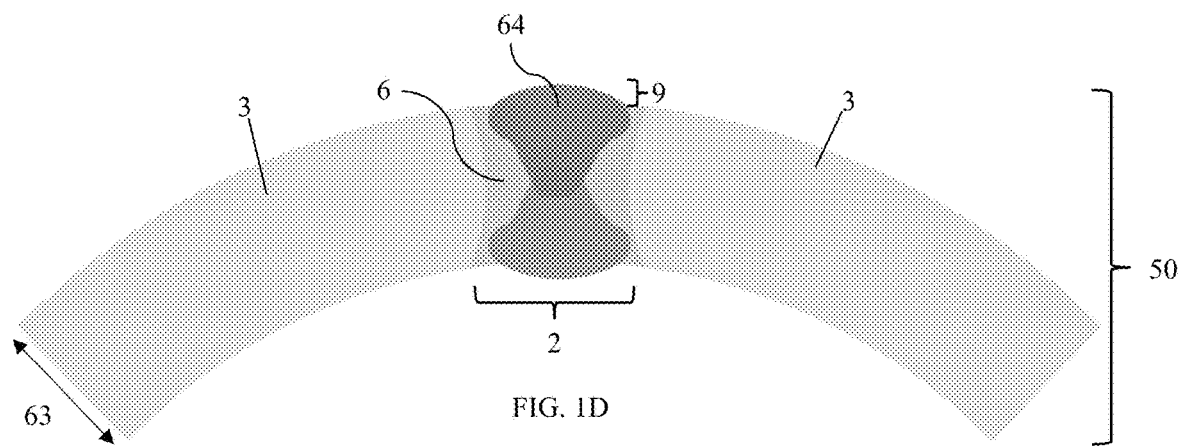
Figure 1E:
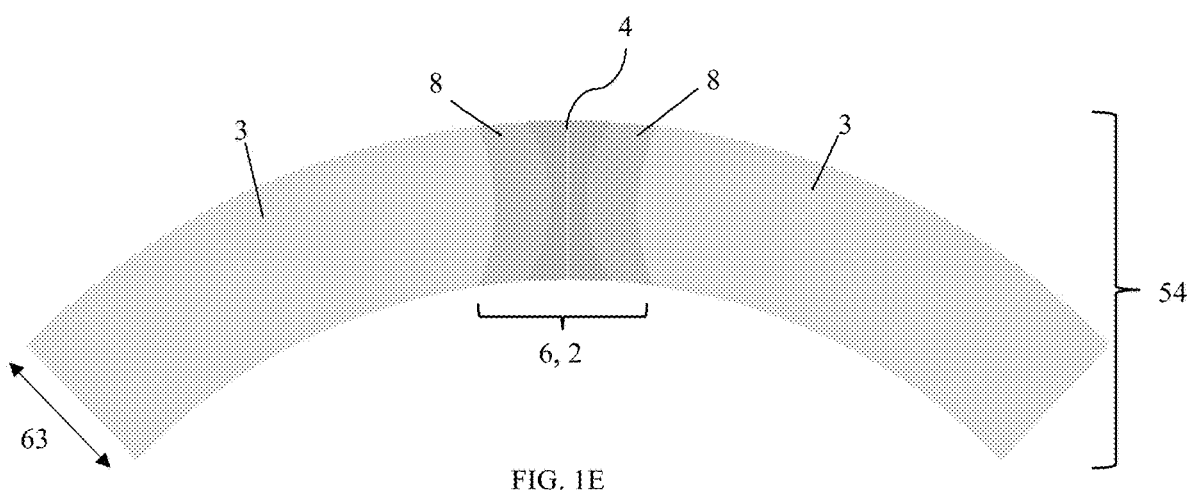

According to the embodiments in the present invention, a formed object 1 contains one or more welds 2, with base material 3 regions that are away from the welds 2 representing material that was not influenced by the joining process. FIG. 1A shows an embodiment of a formed object 1, which is manufactured by bending an initially flat plate into a cylinder, and then making a weld 2 along the length of the formed object 1 to join the opposing sides of the plate into a closed pipe. The welding process used to create the weld 2 on the formed object 1 can vary, with specific embodiments shown in FIGS. 1B-1E. A weld 2 will generally consist of a bondline 4 where the opposing edges of the formed object meet, which is surrounded by a heat-affected-zone (HAZ) 6 that represents a region of material in the weld 2 that has experienced changes in mechanical properties, microstructure, chemistry, and/or internal stresses as a result of the joining process. The weld 2 is surrounded by base material 3 that is outside of the weld 2 and has not experienced any changes as a result of the joining process. FIG. 1B shows an embodiment of an electric-resistance-welded (ERW) 51 welding process where the weld 2 is manufactured by applying heat and pressure to the opposing faces of the formed object 1. FIG. 1C shows an embodiment of a flash-weld 48 that is manufactured in a similar manner to the ERW 51 pipe, but with excess material that is extruded beyond the inside and outside surface of the pipe during welding that is trimmed into a characteristic weld reinforcement 9 with a rectangular profile 85. FIG. 1D shows an embodiment of a submerged-arc-welded (SAW) 50 welding process where filler weld material 64 is added in-between the opposing sides of the formed object 1 and becomes part of the weld 2. SAW 50 joints can be manufactured as single side SAW (SSAW) or double side SAW (DSAW), but will generally have a weld reinforcement 9 with a rounded profile 86. FIG. 1E shows a weld 2 that has undergone a post-weld-heat-treatment (PWHT) 8 that will normalize differences in material properties within the weld 2 and surrounding base material 3, and results in a larger HAZ 6 size. An effective PWHT 8 is attributed to a weld 2 with improved mechanical performance and durability. Additional embodiments of formed objects 1 with welds 2 are not limited to those shown in FIGS. 1A-1E, but also includes formed objects 1 with butt-joints, corner joints, t-joints, lap joints, and edge joints where the weld 2 can be produced using metal inert gas (MIG), tungsten inert gas (TIG), arc welding, plasma arc welding, electron beam welding, laser welding, gas welding, and/or friction stir welding.

Figure 2:
FIG. 2 is a schematic of the general methodology to determine an index of weld quality from multiple observable attributes and measured parameters of a formed object with a weld according to the embodiments of the present invention.
Figure 17:
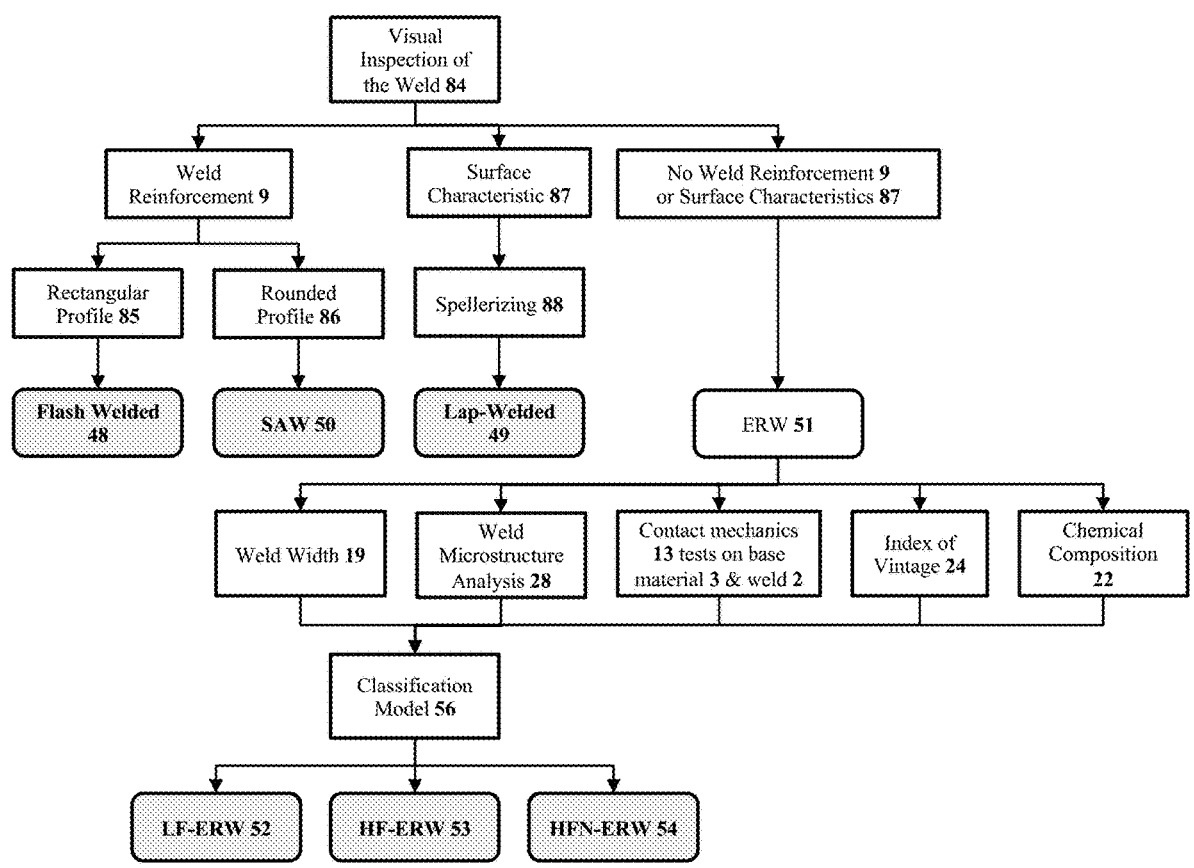
FIG. 17 expands on the schematic represented in FIG. 3 for the methodology to further classify ERW welds as LF-ERW, HF-ERW, and HFN-ERW through additional measurements and parameters according to embodiments of the present invention.
Figure 19A:
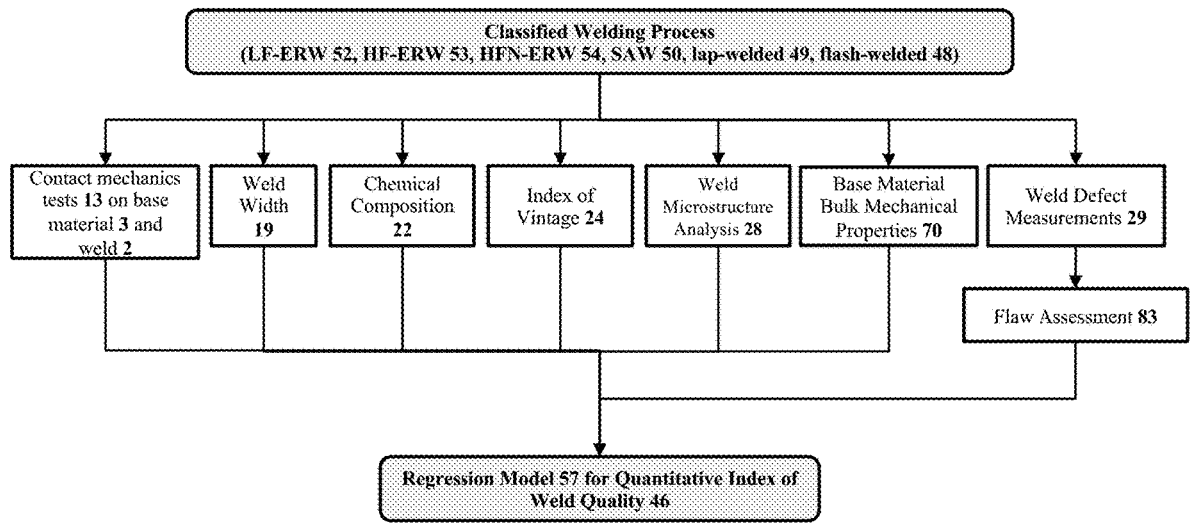
FIG. 19A is a schematic of the methodology to implement a regression model for the quantitative index of weld quality according to embodiments of the present invention and FIG.

Referring to FIG. 2, the methods in embodiments of this invention allow for providing an index of weld quality 46 through the consideration of multiple measurements on a provided formed object with a weld 90. In some embodiments, one or more of these measurements may be nondestructive measurements that do not jeopardize the function of the formed object 1, and therefore can be performed directly on the formed object 1 and weld 2 without changing service conditions. The method further involves performing one or more contact mechanics tests 94 to measure a base material surface mechanical property 78 and to measure a weld surface mechanical property 76. The method then involves determining a relative difference in surface mechanical property 80 between the measured values. The method further involves the measurement of a weld width 96 which provides an indication of a characteristic size of the weld 2. The determined relative difference in surface mechanical property 80 is combined with the measured weld width 96 to evaluate the weld 82 in order to provide an index of weld quality 46. In some embodiments, the inputs are used to develop a predictive model 98 which is then used to evaluate the weld 82. The predictive model 55 can be a classification model 56 (as shown in FIG. 17) or regression model 57 (as shown in FIG. 19A) that relates the measurements collected on the provided formed object with a weld 90 to a traditional index of weld quality 46 determined with standardized tests. Some embodiments further include measurements of additional formed object measurements 81 related to the formed object 1 and weld 2 that can be collected and used to increase accuracy and reduce uncertainty when evaluating the weld 82 and providing an index of weld quality 46. These additional measurements may include the chemical composition 22 of the base material 3 and/or weld 2, an index of vintage 24 of the formed object 1, a weld microstructure analysis 28 to examine changes in microstructure properties, weld defects 29, and/or base material bulk mechanical properties 70. Specific embodiments of these parameters are described below with respect to FIGS. 17 and 19A.

Referring also to FIG. 2, the provided index of weld quality 46 for the provided formed object with a weld 90 can describe the mechanical strength, fracture toughness, ductility, bond quality, and/or durability of the weld 2. These are traditionally measured using standardized methods that have been developed through industry organizations such as American Society for Testing and Materials, American Society of Mechanical Engineers, American Society of Civil Engineers, American Petroleum Institute, American Institute of Aeronautics and Astronautics, and United States Military Standards. Specific embodiments that provide a direct quantitative measurement of an index of weld quality 46 include fracture toughness evaluation based on the measured stress intensity factor (K), J-integral (J), and/or crack-tip-opening-displacement (CTOD), Charpy V-Notch (CVN) or Izod impact testing of the weld 2 to measure the absorbed energy, tensile testing of coupon specimens containing the weld 2 to evaluate strength and ductility of the weld 2 and surrounding base material 3, and fatigue testing of specimens containing the weld 2 to evaluate the resistance of the weld 2 and surrounding base material 3 to the growth of a crack under cyclic loading. These measurements provide data on the material capacity of the weld 2, which can be combined with flaw assessment 83 from geometrical data of weld defects 29 (as described below with respect to FIG. 19A) to evaluate the capacity, risk, and remaining lifetime of the formed object 1 with a weld 2. Indirect measurements of an index of weld quality 46 include the determination of the welding process used to manufacture the weld 2, vintage of the weld 2, quality of the base material 3, and effectiveness of any PWHT 8 applied after welding.

Detailed Description of the Method

Specific Embodiments of Visual Inspection

Figure 3:
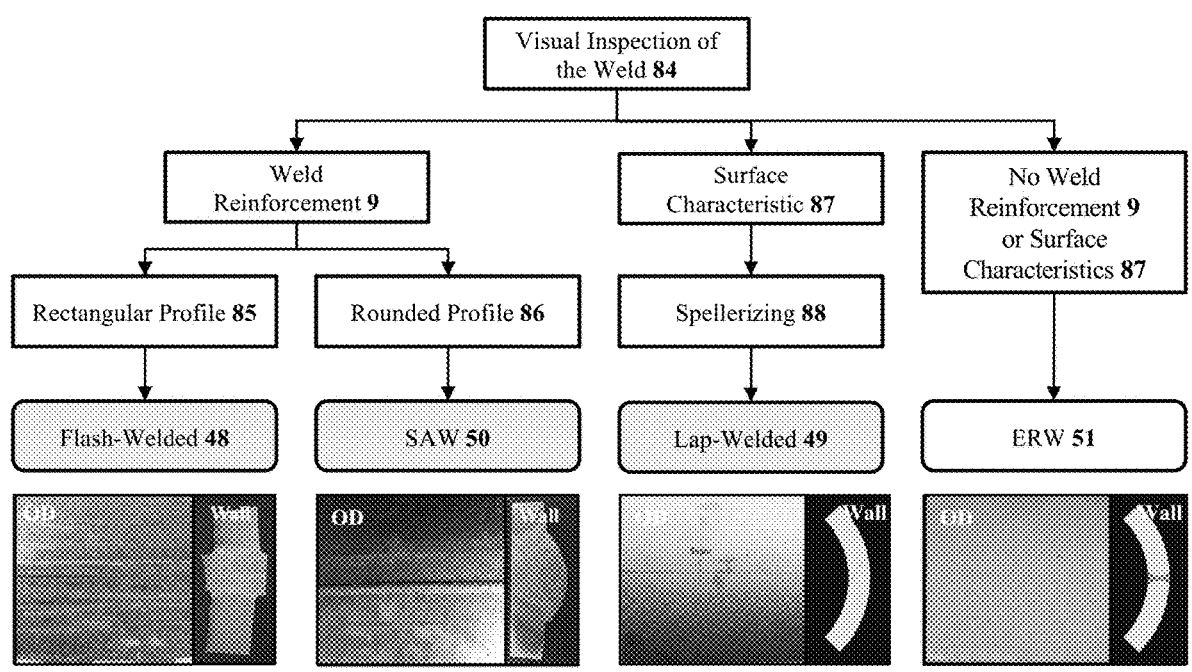
FIG. 3 is a schematic of the methodology to assess surface weld reinforcements and surface characteristics on formed objects with welds to determine an initial classification of a weld according to the embodiments of the present invention.

Visual inspection 84 consists of an examination of the exposed surface of the weld 2 to identify distinguishing features that can be used to determine the type of welding process. The flow chart in FIG. 3 can be used to distinguish between flash-welded 48, SAW 50, lap-welded 49, and ERW 51 welds 2. A flash-weld 48 has a rectangular profile 85 weld reinforcement 9 on both the inner and outer face of the formed object 1. A SAW 50 joint has a rounded profile 86 weld reinforcement 9 which may be on one or more surfaces of the formed object 1. A lap-welded 49 specimen may exhibit a spellerized 88 surface characteristic 87 with a hatched pattern that is imprinted on the surface of the formed object 1 surrounding the weld 2. Finally, an ERW 51 joint can be identified because the weld 2 will exhibit no weld reinforcement 9 or other surface characteristics 87. In one embodiment, the ERW 51 joint may exhibit some excess flash material near the bondline 4 that is raised beyond the surface of the formed object 1. Additional characterization as described in the following sections is required to further classify an ERW 51 joint as LF-ERW 52, HF-ERW 53, or HFN-ERW 54.

Figures 4A, 4B:
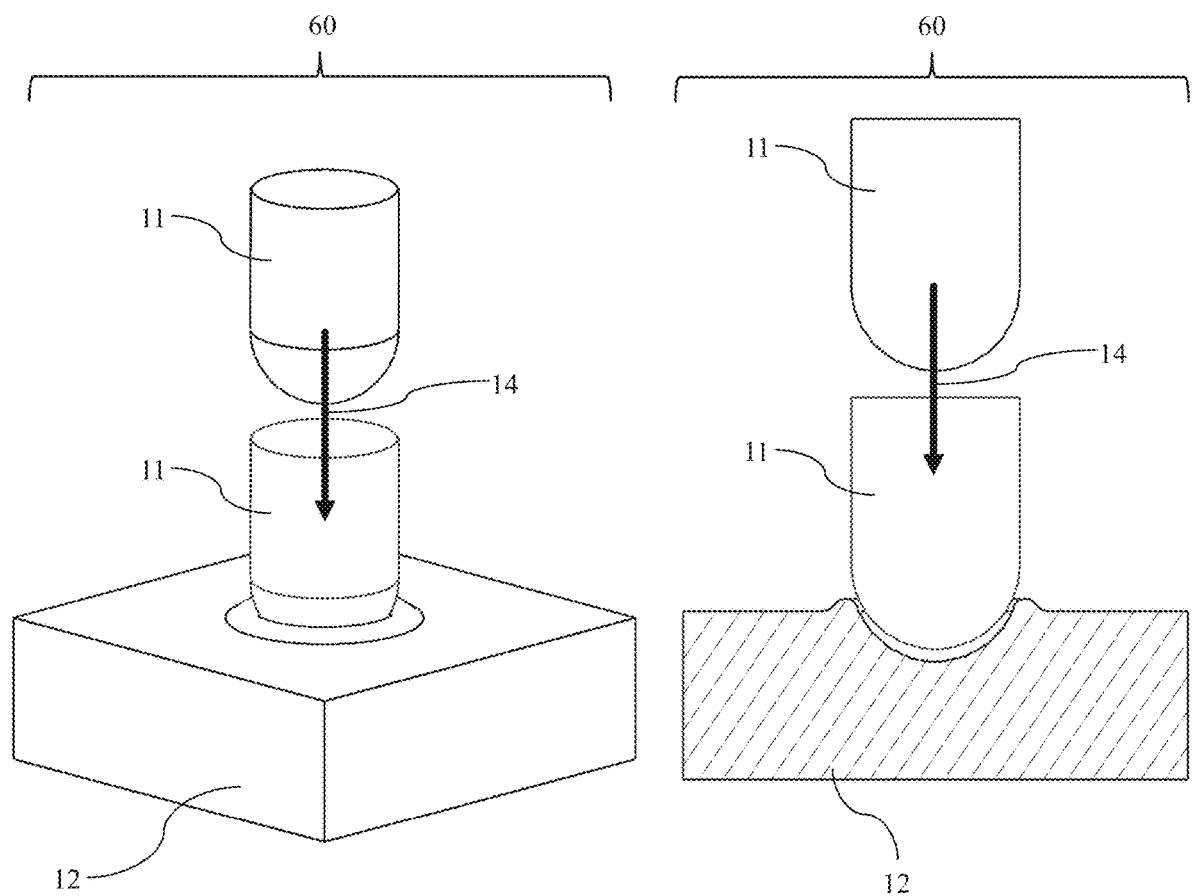
FIGS. 4A-4G are schematics of different embodiments of contact mechanic tests and applications on formed objects with welds according to the embodiments of the present invention.
Figure 4C:
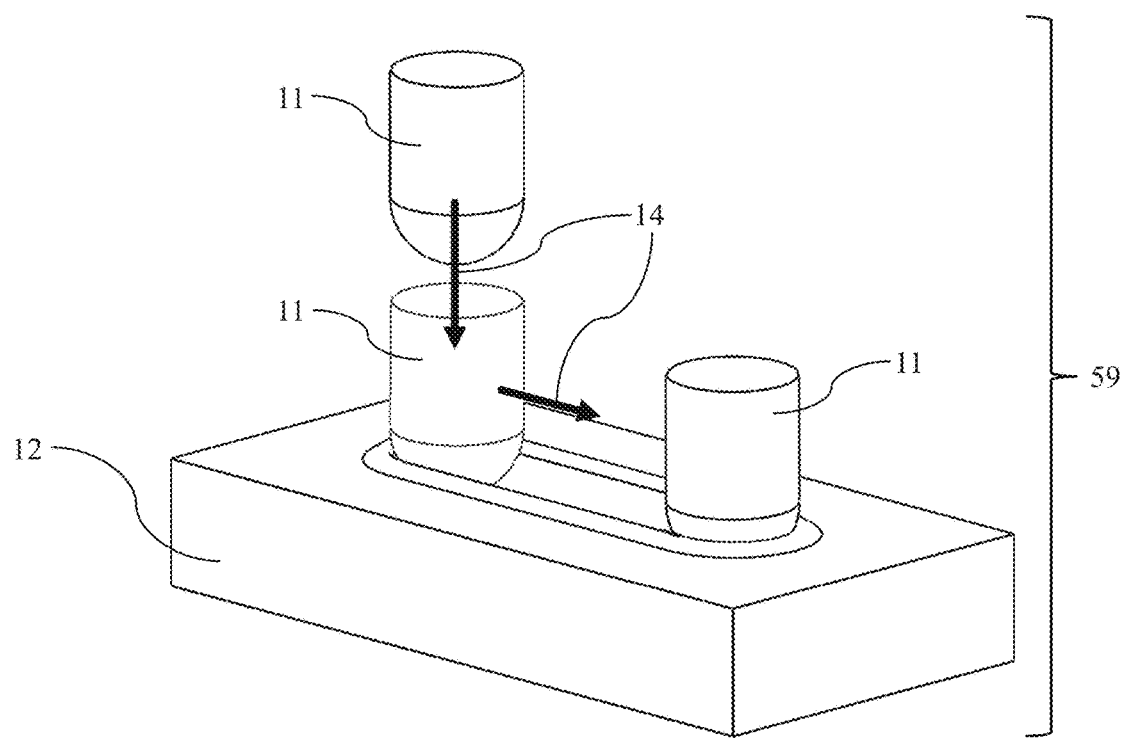
Figure 4D:
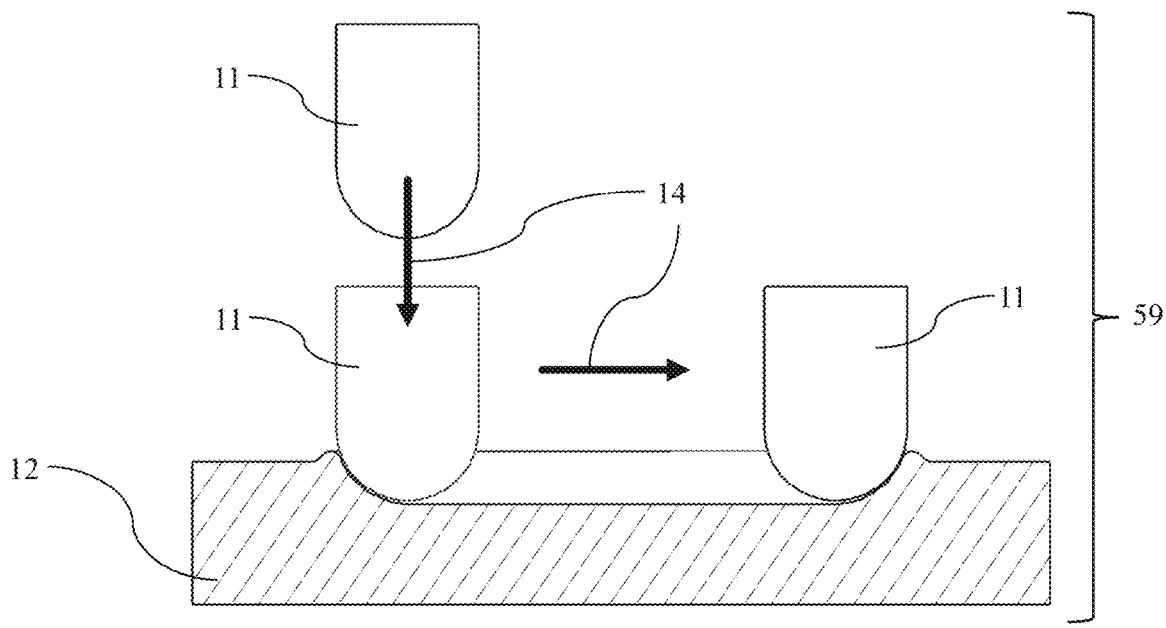

Specific Embodiments of Contact Mechanics Tests for Determining Relative Differences in Surface Mechanical Properties between the Weld and Base Material Referring to FIGS. 4A-4G, contact mechanics tests 13 are performed to determine the surface mechanical properties of materials by using a hard stylus 11 to deform a softer substrate 12 and measuring the material response along the stylus trajectory 14. The generated deformation is localized and, in many applications, does not influence the capacity of the tested object and can therefore be considered as nondestructive. One embodiment of a contact mechanics test 13 is an indentation 60 test where the stylus 11 is pressed perpendicularly into a substrate 12 and then unloaded as illustrated in FIGS. 4A-4B. Another embodiment, known as frictional sliding 59 or scratch testing, is shown in FIGS. 4C-4D, and consists of a stylus 11 that is pressed perpendicularly into the substrate 12 and then slides laterally along a stylus trajectory 14 parallel to the substrate 12 surface to create a residual scratch or groove. Both indentation 60 and frictional sliding 59 tests with a spherical or blunted stylus 11 are used to measure the material hardness which is an indication of a materials resistance to permanent deformation under a known applied load. A different type of material response is measured with the embodiment shown in FIG. 4E, which is a frictional sliding 59 test that is performed with a wedge-shaped stylus 11 that includes a stretch passage 65 along the upstream face to produce a local tensile separation in the substrate 12 as the stylus 11 slides along the surface. This embodiment is used to measure the geometry of a fractured ligament 66 that remains from tensile separation of substrate 12 material within the stretch passage 65. The fractured ligament height is correlated to the fracture toughness or crack-tip-opening-displacement (CTOD) of the substrate 12.

In embodiments of this invention, contact mechanics tests 13 are used to measure the variation in surface mechanical properties across the weld 2. For a formed object 1 that is a cylinder, tube, or pipe with a longitudinal weld 2 this can be accomplished by performing a contact mechanics test 13 on the surface of the formed object 1 in the circumferential direction, such as shown in FIG. 4F. In one embodiment shown in FIG. 4F, this is accomplished by performing a frictional sliding 59 test that starts in the base material 3 and then slides through the weld 2 and into the base material 3 on the opposing side of the weld 2. Frictional sliding 59 allows for hundreds of measurements to be collected along the length of the stylus trajectory 14 to monitor changes in the material response with high spatial resolution. The stylus 11 used could have a spherical or blunted geometry to measure the substrate 12 hardness, or a wedge-shaped stylus 11 with a stretch passage 65 could be used to measure substrate 12 fracture toughness and CTOD. An embodiment for measuring mechanical variation with indentation 60 testing is shown in FIG. 4G, where an array of indentation 60 tests is performed so that the surface mechanical properties can be mapped throughout the base material 3 and weld 2.

Weld surface mechanical property profiles are used to visualize and determine relative differences in surface mechanical properties along a stylus trajectory 14 that includes the base material 3 and weld 2. The weld surface mechanical property profile may be used to evaluate relative differences between the weld 2 and base material 3. In one embodiment, a spherical or blunted stylus 11 is used to measure hardness, and the resulting weld surface mechanical property profile is a weld hardness profile. In another embodiment, a wedge-shaped stylus 11 with a stretch passage 65 is used to measure the geometry of a fractured ligament 66, and the resulting weld surface mechanical property profile is a weld fractured ligament profile. In another embodiment, the relative difference in surface mechanical properties 80 in the base material 3 and weld 2 are determined from multiple tests that do not include both the base material 3 and weld 2.

Figure 4F:
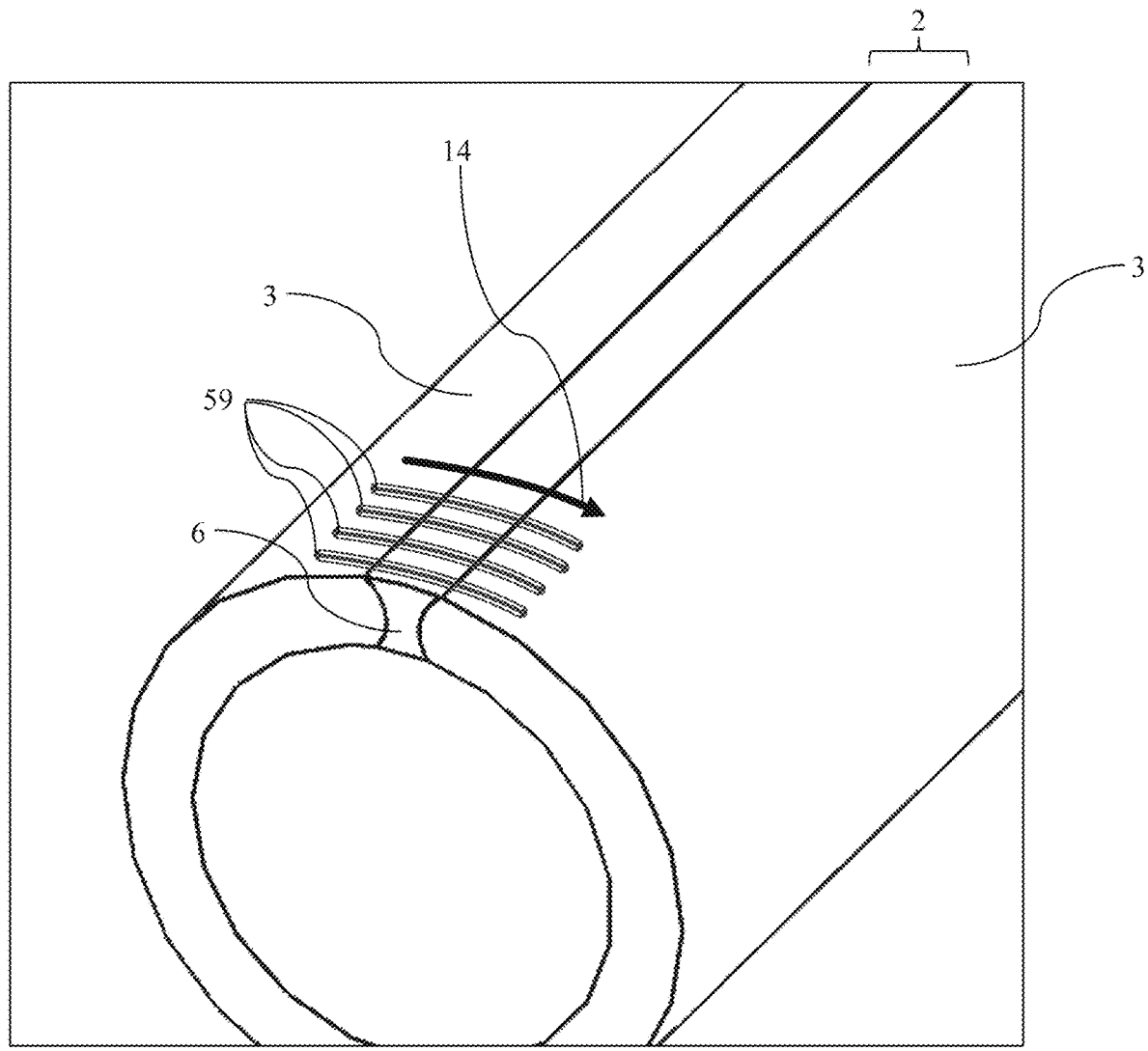
Figure 5A:
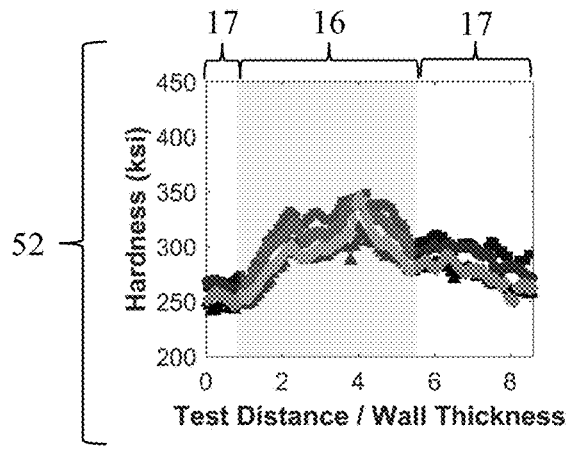
FIGS. 5A-5E are depictions of weld hardness profiles from frictional sliding contact mechanics tests across the welds of formed objects according to the embodiments of the present invention.
Figure 5B:
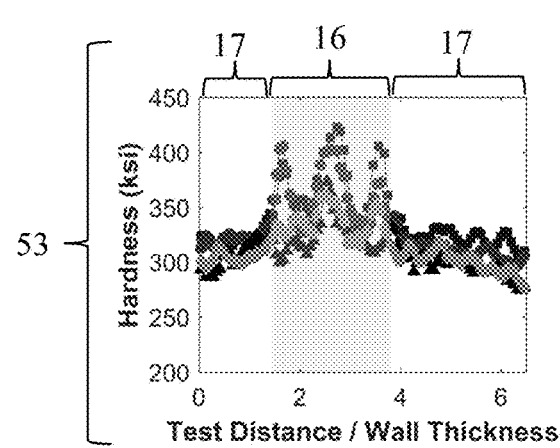
Figure 5C:
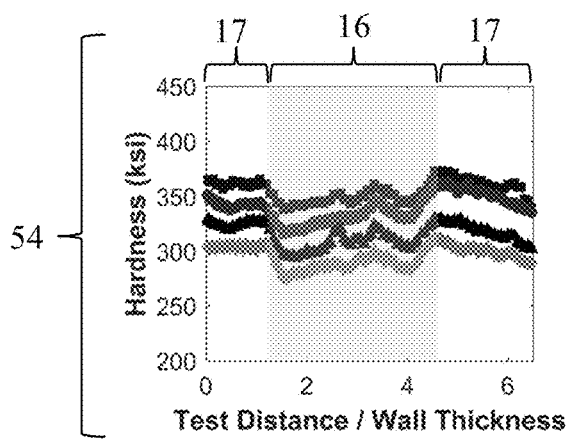
Figure 5D:
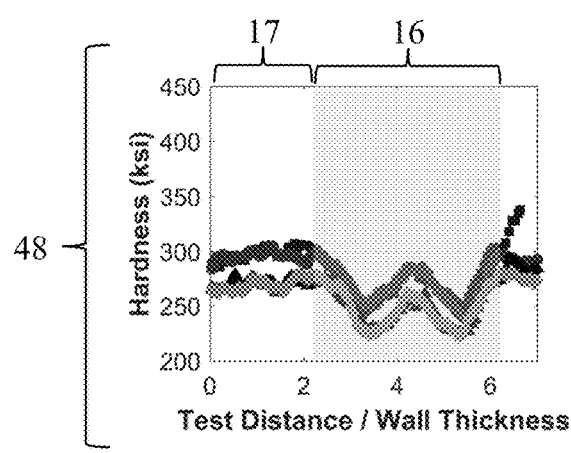
Figure 5E:
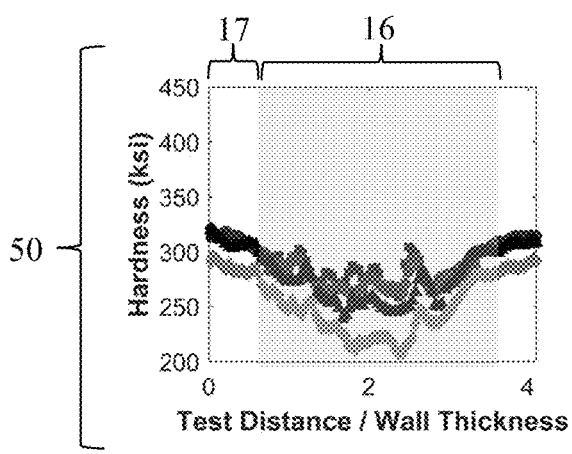
Figure 6A:
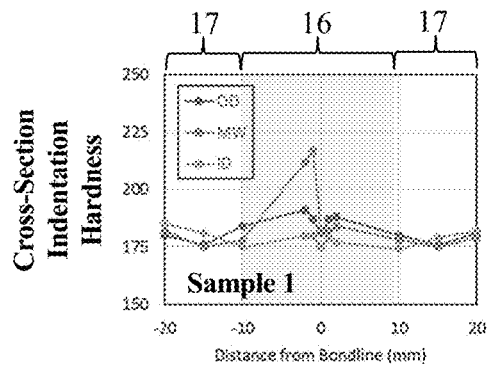
FIGS. 6A-6H are depictions of weld hardness profiles from indentation and frictional sliding contact mechanics tests across the welds of formed objects according to the embodiments of the present invention.
Figure 6B:
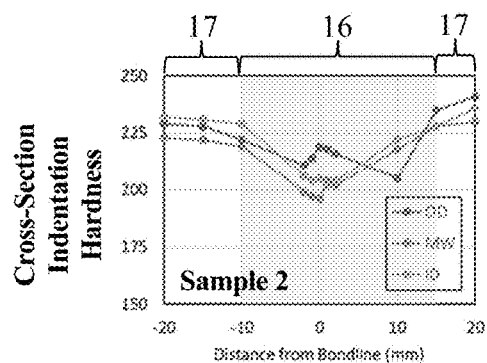
Figure 6C:
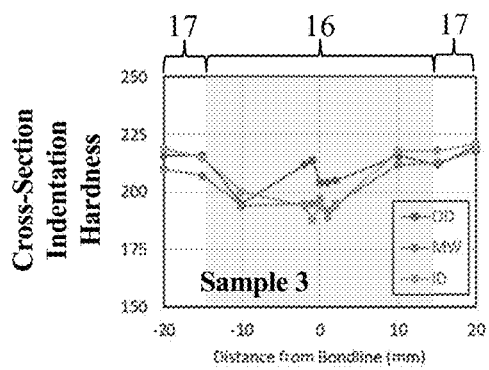
Figure 6D:
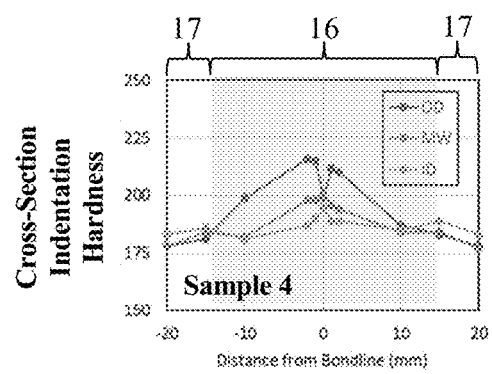
Figure 6E:
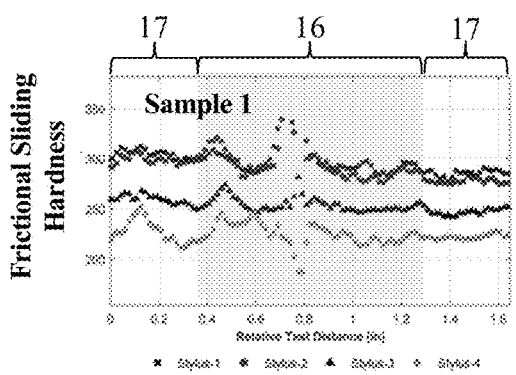
Figure 6F:
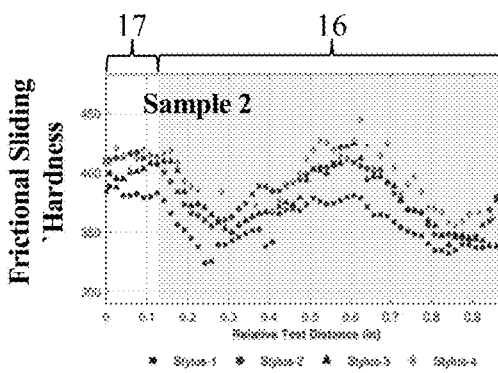
Figure 6G:
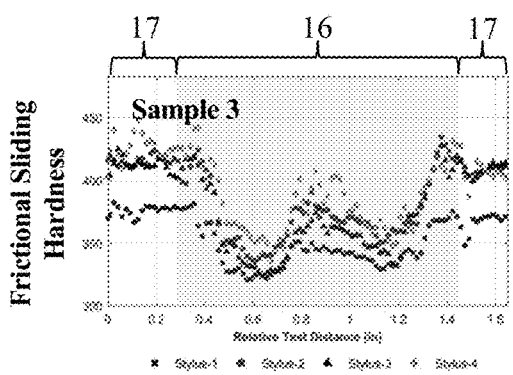
Figure 6H:
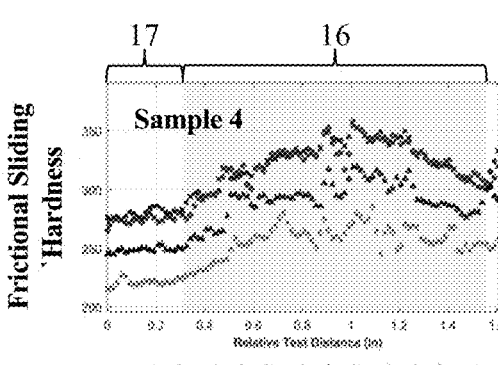

Representative weld hardness profiles obtained from frictional sliding 59 tests for different welding processes is shown in FIGS. 5A-5E. For these embodiments, four styluses 11 were used to collect weld hardness profiles along the length of a frictional sliding 59 test that was conducted using the approach shown in FIG. 4F. The weld hardness profiles in these embodiments were used to identify the weld hardness 16, and base material hardness 17. For the LF-ERW 52 pipe in FIG. 5A, the increase in weld hardness 16 spans across the entire weld 2 without a sharp peak at the bondline 4. The HF-ERW 53 pipe in FIG. 5B exhibits a significant spike in weld hardness 16 at the bondline 4, whereas a normalized HFN-ERW 54 pipe in FIG. 5C shows a reduced weld hardness 16 compared to the surrounding base material hardness 17 as a result of an effective PWHT 8. The flash-welded 48 pipe in FIG. 5D shows a decrease in weld hardness 16 compare to the base material hardness 17, with almost no change at the bondline 4. A SAW 50 pipe in FIG. 5E shows a decrease in weld hardness 16 through the entire weld 2. These embodiments demonstrate the ability of weld hardness profiles to distinguish between base material 3 and weld 2 regions from the measured hardness. The embodiments also show the influence of different welding processes and the application of a PWHT 8 on the surface mechanical properties.

Additional embodiments of weld hardness profiles are shown in FIGS. 6A-6H for tests on four different HFN-ERW 54 welds 2. FIGS. 6A-6D are measurements collected with an array of indentations 60 performed on a transverse cross-section containing the weld 2. FIGS. 6E-6H are measurements collected with a frictional sliding 59 test on the outer surface of a formed object 1 with four styluses 11. Each weld 2 was tested with both the indentation 60 test and frictional sliding 59 test method, with the generic sample name shown on the plots for comparison. The embodiments with the indentation 60 test measurements shown in FIGS. 6A-6D indicate that weld hardness profiles exhibit the same trends for tests performed on the formed object 1 outer diameter (OD), mid-wall (MW), and inner diameter (ID). These trends also agree with the frictional sliding 59 test weld hardness profiles shown in FIGS. 6E-6H, but the weld hardness profiles from frictional sliding 59 tests have many more hardness measurements because indentation 60 tests require a minimum separation between adjacent tests, resulting in a lower spatial resolution. These HFN-ERW 54 samples demonstrate the significant differences in weld hardness profiles that can be obtained even for welds 2 formed with the same welding process as a result of varying effectiveness of the PWHT 8.

Figure 4E:
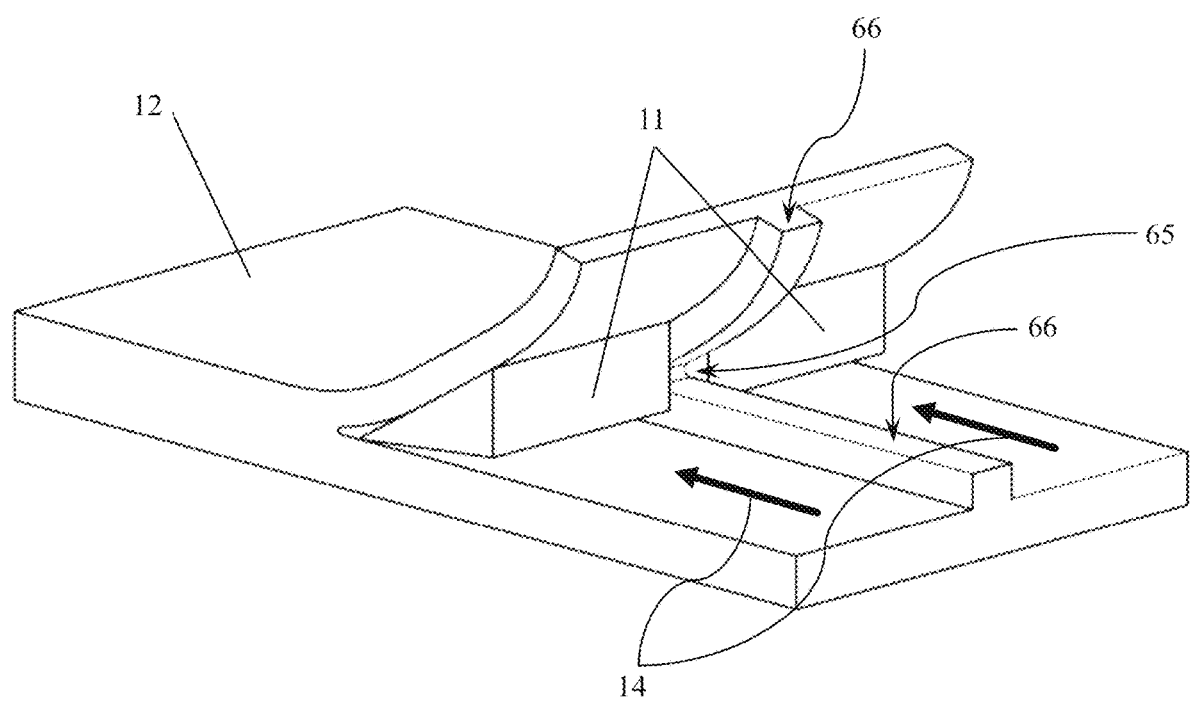
Figure 4G:
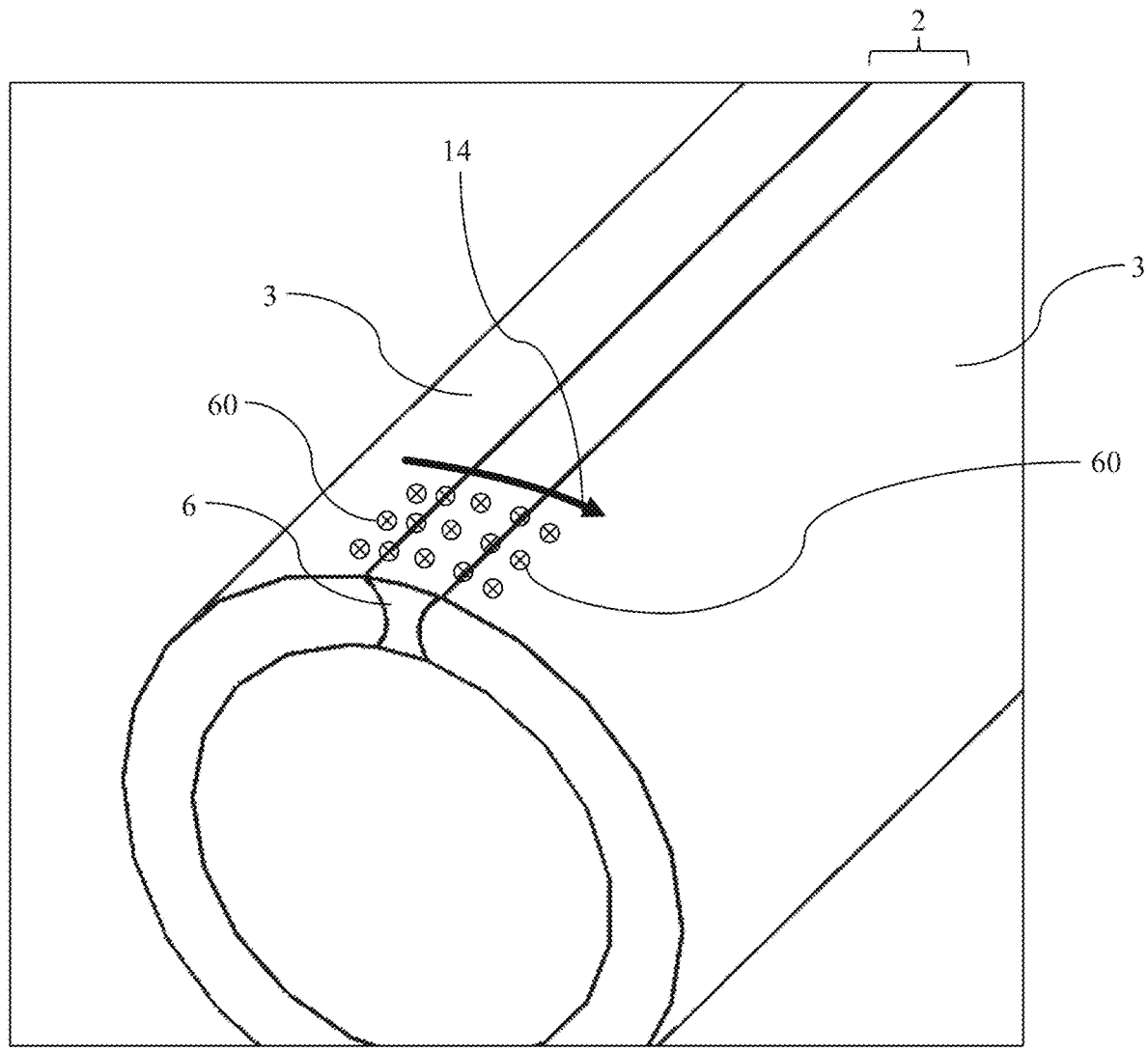
Figure 7:
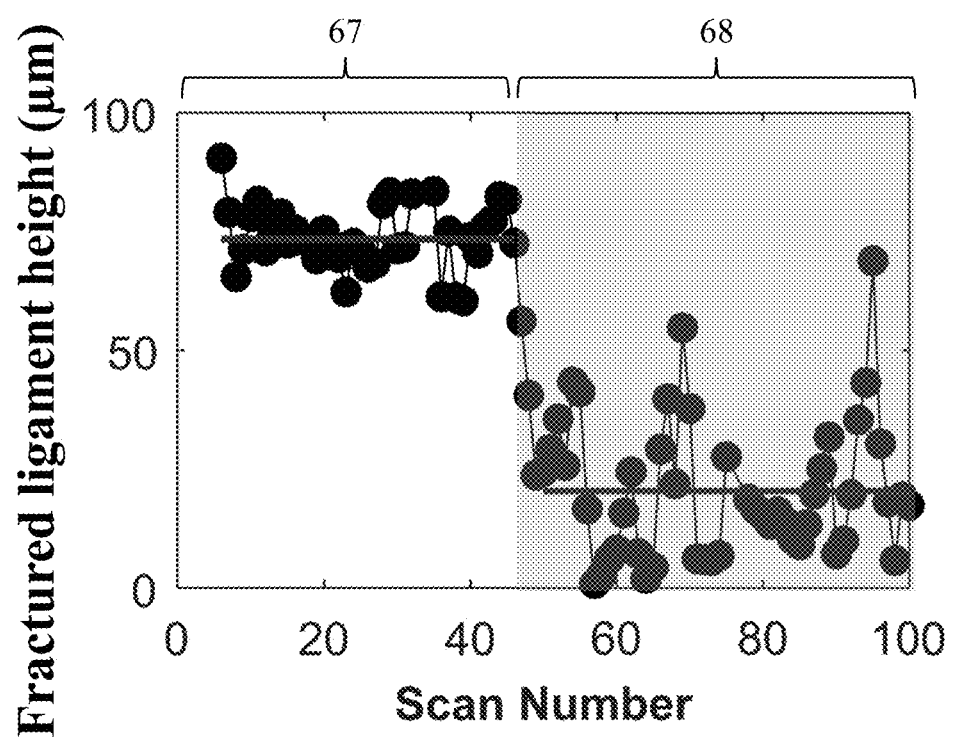
FIG. 7 is a depiction of a weld fractured ligament profile from a frictional sliding contact mechanics test across the weld of a formed object according to the embodiments of the present invention.

An embodiment of a weld fractured ligament profile is shown in FIG. 7 for a friction sliding 59 test using a wedge-shaped stylus 11 with a stretch passage 65, such as shown in FIG. 4E. The weld fractured ligament profile can be used to identify the base material fractured ligament 67 and weld fractured ligament 68. The large reduction in weld fractured ligament 68 shown in FIG. 7 indicates a decrease in the weld 2 material fracture toughness and CTOD compared to the base material 3.

In another embodiment, the fractured ligament profile can be converted to a fracture toughness or CTOD profile by using predictive relationships. In another embodiment, a hardness profile is converted to a tensile yield strength profile, ultimate tensile strength profile, or tensile ductility profile using predictive relationships that allow for the conversion of hardness measurements on multiple styluses 11 to an equivalent tensile stress-strain behavior. In another embodiment, both hardness profiles and fractured ligament profiles are collected on the same weld 2 to determine relative differences in tensile strength, ductility, and fracture toughness. These properties can be used to determine capacity of formed objects 1 for different engineering applications and potential failure modes and provide an important input for providing an index of weld quality 46.

Figure 8A:
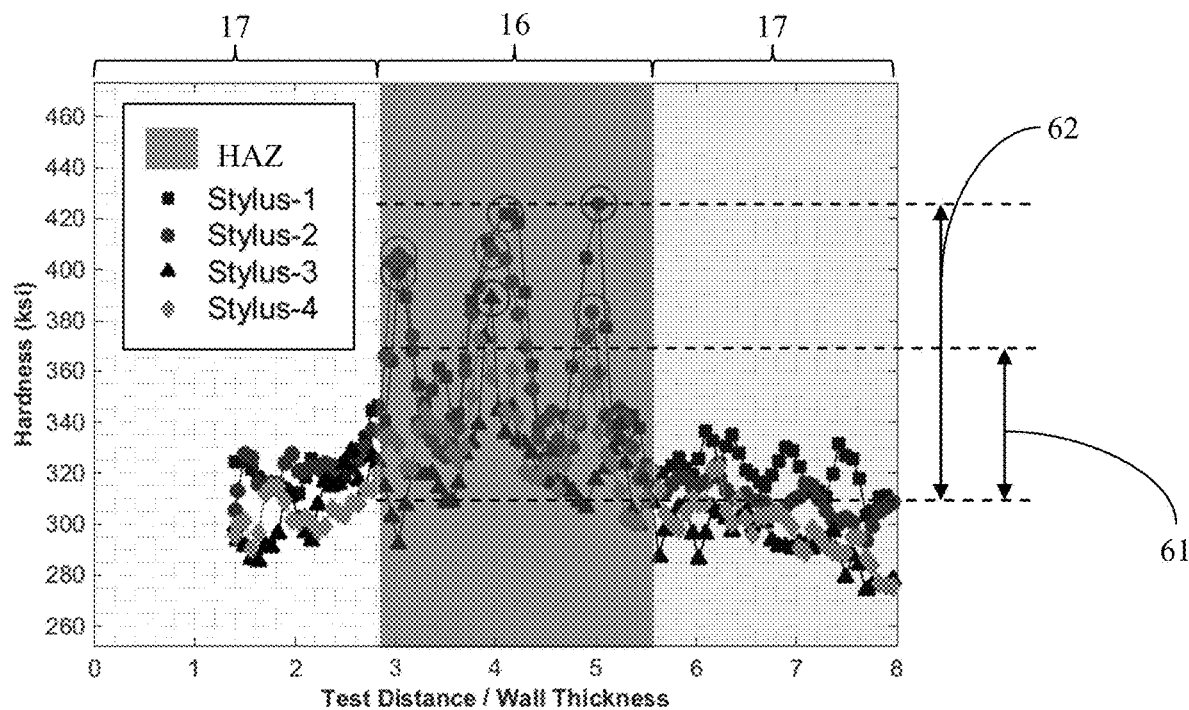
FIG. 8A is the analysis of a weld hardness profile to determine relative changes in surface mechanical properties between the weld and base material according to the embodiments of the present invention.
Figure 8B:
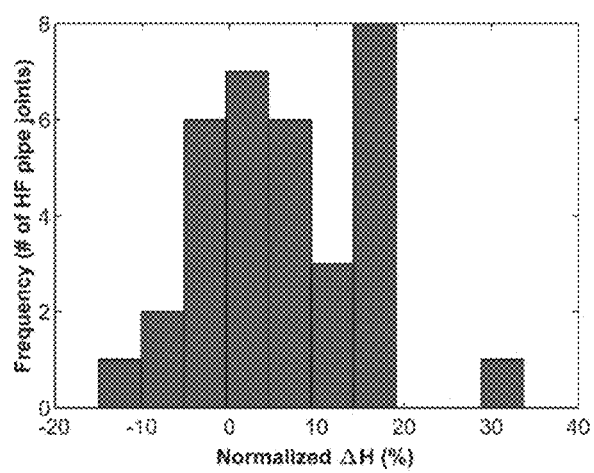
FIG. 8B is a histogram of data collected with this approach on thirty-six formed objects with welds that have undergone a post-weld-heat-treatment.

Weld surface mechanical property profiles can be analyzed to quantify relative differences across the weld 2 and base material 3. An embodiment is shown in FIG. 8A for a frictional sliding test with spherical styluses 11 on a HF-ERW 53 weld 2. The weld hardness 16 and base material hardness 17 regions are identified from the weld hardness profile, which can be used to determine multiple parameters that quantify the relative differences. One embodiment is the average relative hardness difference 61 between the average weld hardness 16 and the average base material hardness 17. Another embodiment is the local peak relative hardness difference 62 based on examination of local maxima and minima in the weld hardness 16 with respect to a representative base material hardness 17. These relative changes can be normalized by the average base material hardness 17 to calculate a percent change. A histogram of the normalized average relative hardness differences for thirty-six HF-ERW 53 and HFN-ERW 54 formed objects is shown in FIG. 8B. These results indicate a bi-modal distribution, with one peak centered at normalized average relative hardness differences of ±15% that is attributed to HF-ERW 53 welds, and another peak centered near normalized average relative hardness differences of 0% that is attributed to HFN-ERW 54 welds. A lower value of normalized average relative hardness differences is associated with a more effective PWHT 8 that was able to normalize the microstructure and relieve residual stresses in the weld 2. These relative differences have a large influence when determining an index of weld quality 46 because they reflect changes in the mechanical properties of the formed object 1 as a result of the welding process.

Specific Embodiments of Measuring Weld Width

Figure 9A:
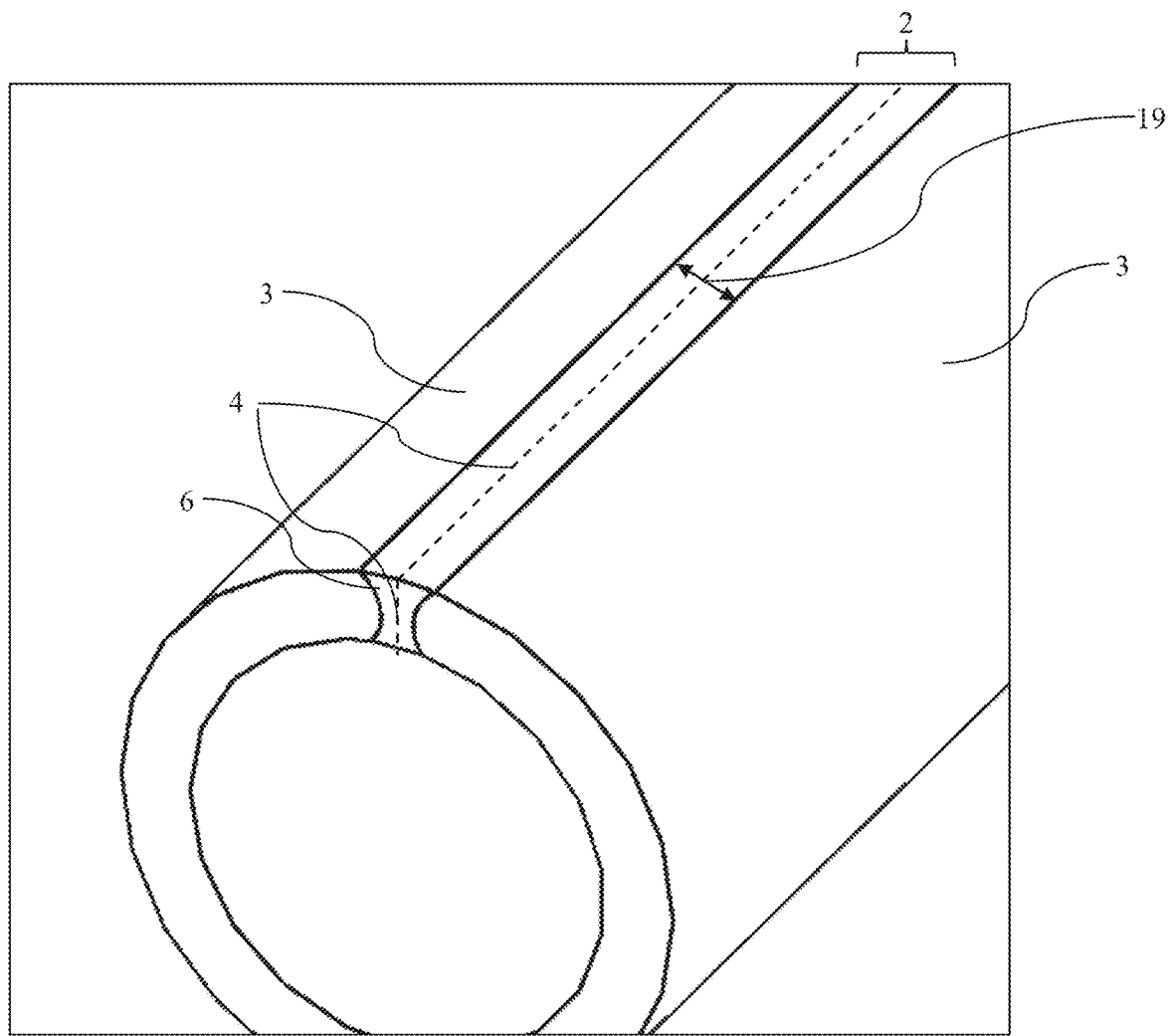
FIGS. 9A-9B are schematics of weld width measurements according to the embodiments of the present invention.
Figure 9B:
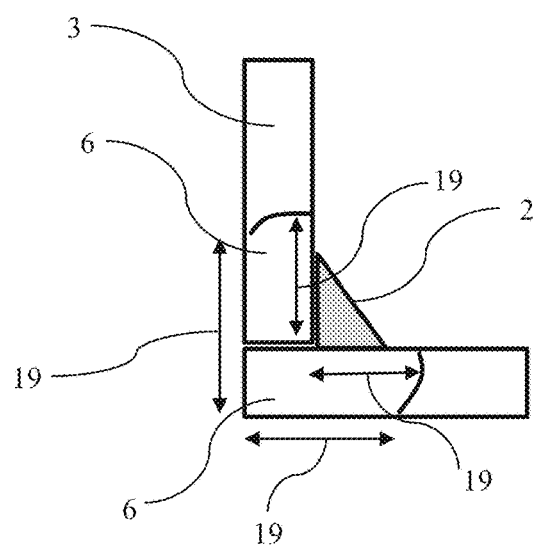

The size of the HAZ 6 in a weld 2 reflects the welding process used and welding parameters. These welding parameters include the duration, temperature, heat flux, pressure, heat input source, and geometry of the formed object 1. As a result, the measurement of a characteristic weld width 19 provides critical information that reflects the manufacturing conditions, and which may allow for a better determination of the provided index of weld quality 46. The appropriate orientation and location for a weld width 19 measurement depends on the welding process, weld 2 geometry, formed object 1 geometry, and accessibility. In general, the weld width 19 should be perpendicular to the plane of the joined edges of the formed object 1 and should be on an exposed surface that can be examined using appropriate methods. For embodiments where the formed object 1 is a cylinder, tube, or pipe with a longitudinal weld 2, the weld width 19 is in the circumferential direction as shown in FIG. 9A. The weld width 19 measurement could be on the inside or outside of the formed object 1 depending on whether an internal or external inspection was being conducted. The weld widths 19 for a fillet weld is shown in FIG. 9B for a corner joint. Multiple weld width 19 measurements may be collected on each component of the connection to assess the influence of each leg of the weld 2. In another embodiment, only one side of the weld 2 may be examined due to accessibility constraints. For both embodiments in FIGS. 9A-9B, one or more measurements of the weld width 19 can be collected along the length of the weld 2.

Figure 10A:
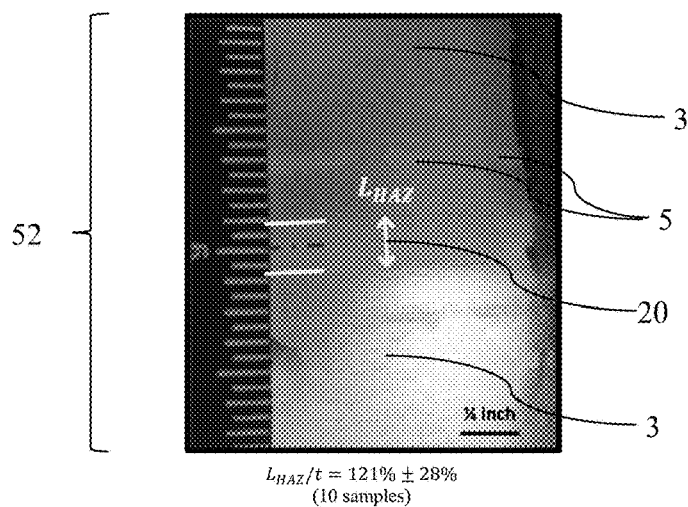
FIGS. 10A-10C are photographs showing etched weld width measurements across the outer surface of the formed objects according to the embodiments of the present invention.
Figure 10B:
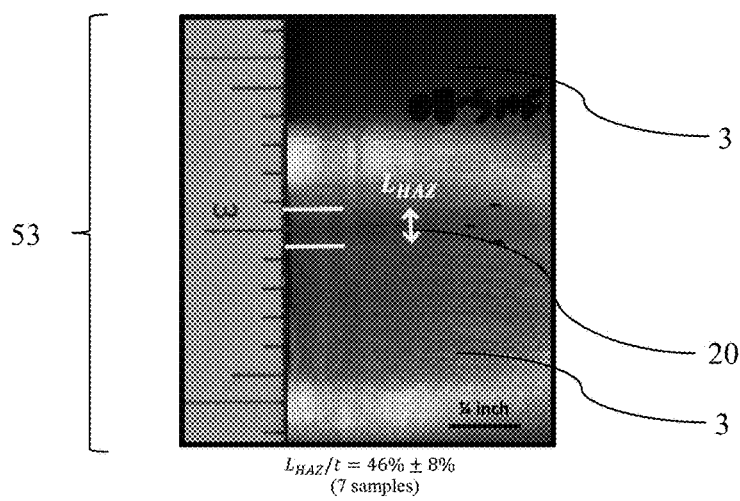
Figure 10C:
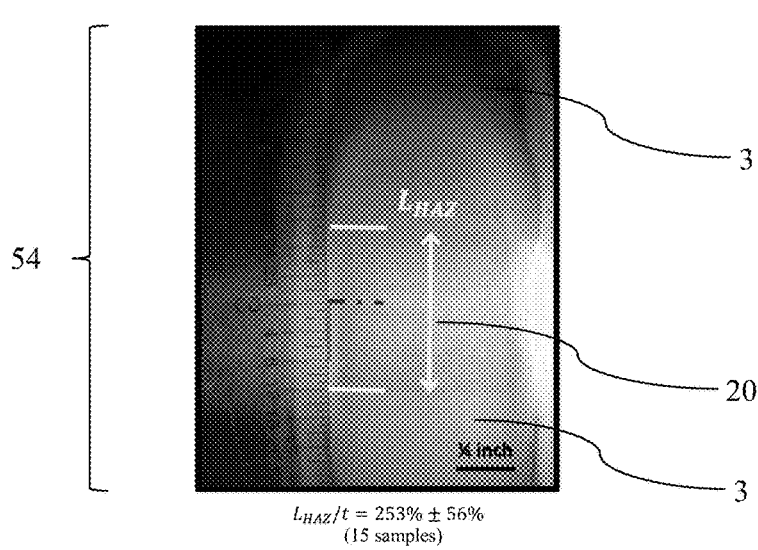
Figure 10D:
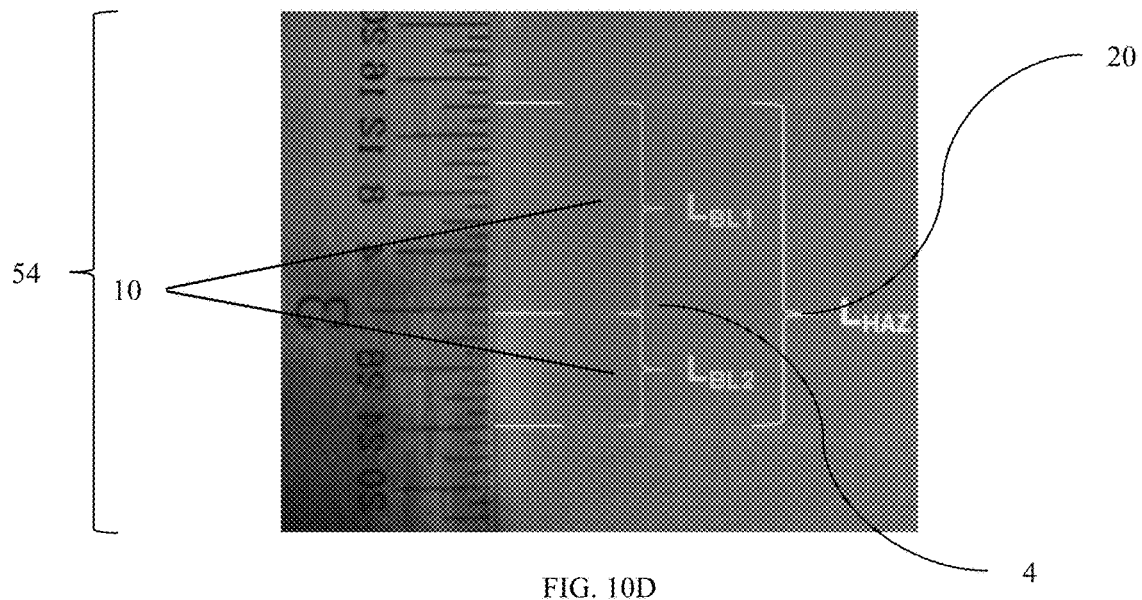
FIG. 10D is a photograph showing an asymmetric heat-affected-zone (HAZ).

One method of measuring the weld width 19 is to polish the surface near the weld 2, and apply a corrosive solution, or etchant, to the outer surface of the formed object 1 in a region that includes a portion of the weld 2 and surrounding base material 3. This procedure will result in the discoloration of surface material that is part of the HAZ 6, and can be used to identify the location and geometry of the weld 2, bondline 4, and other surface characteristics 87 such as contact points 5 that are used for some LF-ERW 52 and HF-ERW 53 welding processes. The etchant should be applied to the surface for a short duration, e.g., on the order of ten seconds, before being washed away from the surface. The etching procedure will vary depending on the properties of the base material 3 and weld 2 material, and the conditions of application including the quality of the surface polish, cleanliness of the surface, environmental temperature and humidity, concentration of the etchant, and duration of application of the etchant. For additional contrast of the etched material, Fry's Reagent can be applied to act as a stain that further defines features of the weld 2. Representative images of the etched weld 2 after implementation of this procedure on ERW 51 welds 2 is shown in FIGS. 10A-10C, with the bondline 4 shown by a dashed line and the extents of the etched weld 2 shown by solid lines. The etched weld width 20 for a LF-ERW 52, HF-ERW 53, and HFN-ERW 54 weld 2 is also shown. Testing of many ERW 51 samples with this method has shown that dividing the etched weld width 20 by the formed object 1 wall thickness 63 determines a normalized etched weld width 74 that is representative of the ERW 51 welding process used. FIG. 10A shows that a typical LF-ERW 52 weld 2 has a normalized etched weld width 74 that is on the order of the formed object 1 wall thickness 63 and which is often surrounded by contact points 5. A typical HF-ERW 53 weld 2 is shown in FIG. 10B and has a narrow normalized etched weld width 74 that is about half of the formed object 1 wall thickness 63. The typical HFN-ERW 54 weld 2 is shown in FIG. 10C and has a very wide normalized etched weld width 74 that is two to three times the formed object 1 wall thickness 63. FIG. 10D shows that the HFN-ERW 54 weld 2 may also be off-centered with respect to the bondline 4, resulting in an asymmetric HAZ 10. An asymmetric HAZ 10 is unique to HFN 54 welds 2 because of the applied PWHT 8, and it is an important consideration for identifying the HFN-ERW 54 welding process.

Figure 10E:
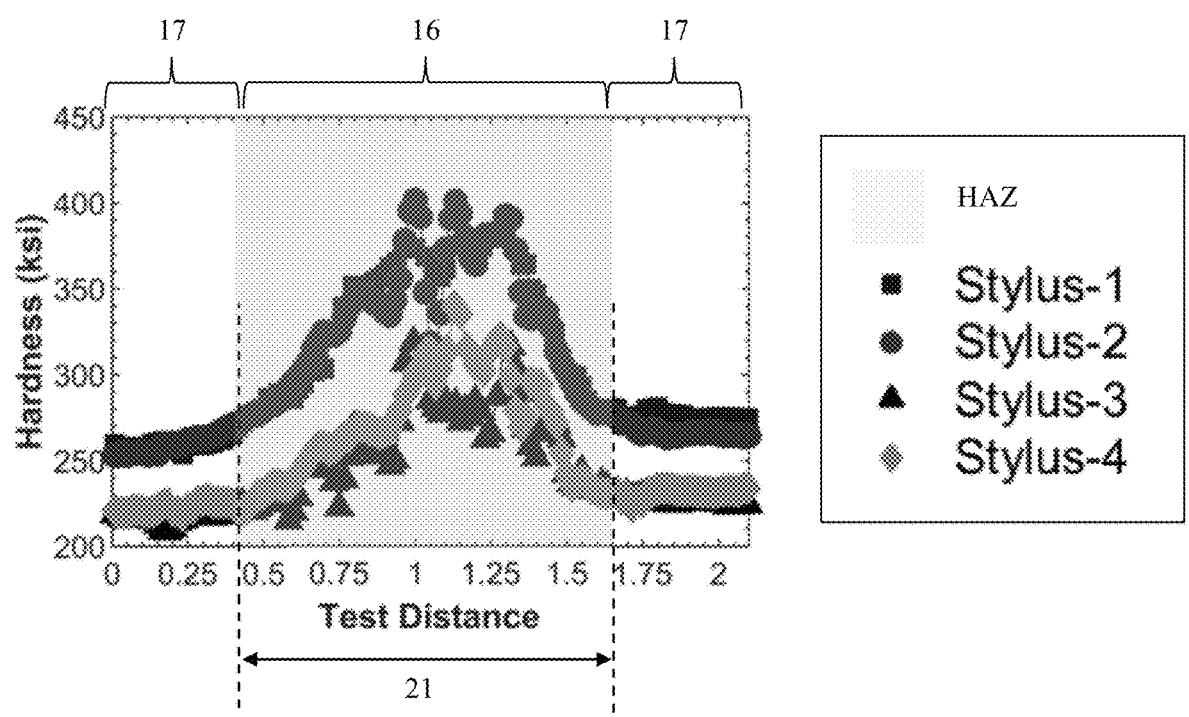
FIG. 10E. is a depiction of a weld hardness profile showing a hardness weld width measurement according to the embodiments of the present invention.

Another method of measuring the weld width 19 is to examine the weld surface mechanical property profile collected from contact mechanics testing 13 where the stylus trajectory 14 includes both the weld hardness 16 and base material hardness 17 on both sides of the weld 2. The relative difference in surface mechanical property 80 measurements along the weld surface mechanical property profile can be used to determine the transition from base material 3 to weld 2, which defines the surface mechanical property weld width 19. This is because the base material 3 will generally show uniform surface mechanical properties with no trends or oscillations, whereas the weld 2 will exhibit large fluctuations in weld surface mechanical properties 76 relative to the base material surface mechanical property 78. An embodiment of this approach is shown in FIG. 10E, where a weld hardness profile was used to determine the hardness weld width 21 based on the weld hardness 16 and base material hardness 17 measurements. In another embodiment, the weld fractured ligament profile could be used to determine the fractured ligament weld width.

Specific Embodiments of Measuring Chemical Composition

Chemical composition 22 reflects the basic atomic structure and plays an important role in determining the mechanical and durability properties of a material. Chemical composition 22 can indicate stable microstructure and precipitation phases, probable sources of environment related defects such as hydrogen embrittlement or sulfur poisoning, and the overall quality of the material based on the presence of different proportions of either beneficial or harmful elements. A weld 2 that was manufactured with low quality base material 3 is more likely to have a lower index of weld quality 46. The chemical composition of the weld 2 and/or filler weld material 64 (as shown in FIG. 1D) also provide further indications of the welding process, cooling conditions, PWHT 8 performance, compatibility with base material 3, and presence of unwanted inclusions phases.

Chemical composition may be measured with a number of available methods. Traditional techniques like Inductively Coupled Plasma Optical Emission Spectroscopy (ICP-OES), Inductively Coupled Plasma Atomic Emission Spectroscopy (ICP-AES), X-ray fluorescence (XRF), X-ray powder diffraction (XRD), and combustion require material to be removed from the formed object and then tested in a laboratory. These techniques can still be used for a nondestructive measurement of chemical composition if burrs or shavings of surface material are removed with a deburring tool resulting in a superficial loss of wall thickness 63 of the formed object 1. Additional hand-held portable devices like spark-OES and SciAps Laser-Induced Breakdown Spectroscopy LIBS can be used to measure chemical composition 22 in-situ on the surface of the formed object 1. These hand-held devices evaluate a smaller volume of material for each test and can therefore be used to investigate differences in the chemical composition 22 in the base material 3 and weld 2.

The results of chemical analysis will provide the weight or volume percentage of each chemical element that was detected. This data can be used to determine the material grade by referencing established industry standards, the microstructure phases 27, and precipitations that are expected to be present in the material especially using carbon, manganese, chromium, and vanadium. Other elements such as sulfur, and phosphorus can also indicate the quality of the material and susceptibility to many sources of corrosion and/or embrittlement. The chemical composition 22 of a steel material can also be used to determine the carbon equivalent, which is a weighted average of the measured chemical components that provides an indication of hardenability and weldability of the steel.

Specific Embodiments of Weld Microstructure Analysis

A material microstructure reflects the basic building blocks of the material that have a significant influence on larger scale material properties. For crystalline materials like steel, aluminum, and copper, the microstructure is composed of grains that can be defined by their size, shape, orientation, texture, and boundaries, as well as chemical phases, inclusions and precipitations.

A material microstructure can be examined by preparing a region on the surface of the formed object 1 by progressively polishing to a mirror finish and then applying an etchant to the prepared region. The etchant should be applied to the surface for a short duration, e.g., on the order of ten seconds, before being washed away from the surface. The etching procedure will vary depending on the properties of the material, and the conditions of application including the quality of the surface polish, cleanliness of the surface, environmental temperature and humidity, concentration of the etchant, and duration of application of the etchant. The etched surface can then be examined by either creating a replica of the microstructure that can be viewed with a desktop microscope, or directly examining the microstructure in-situ with a portable microscope.

Figure 11A:
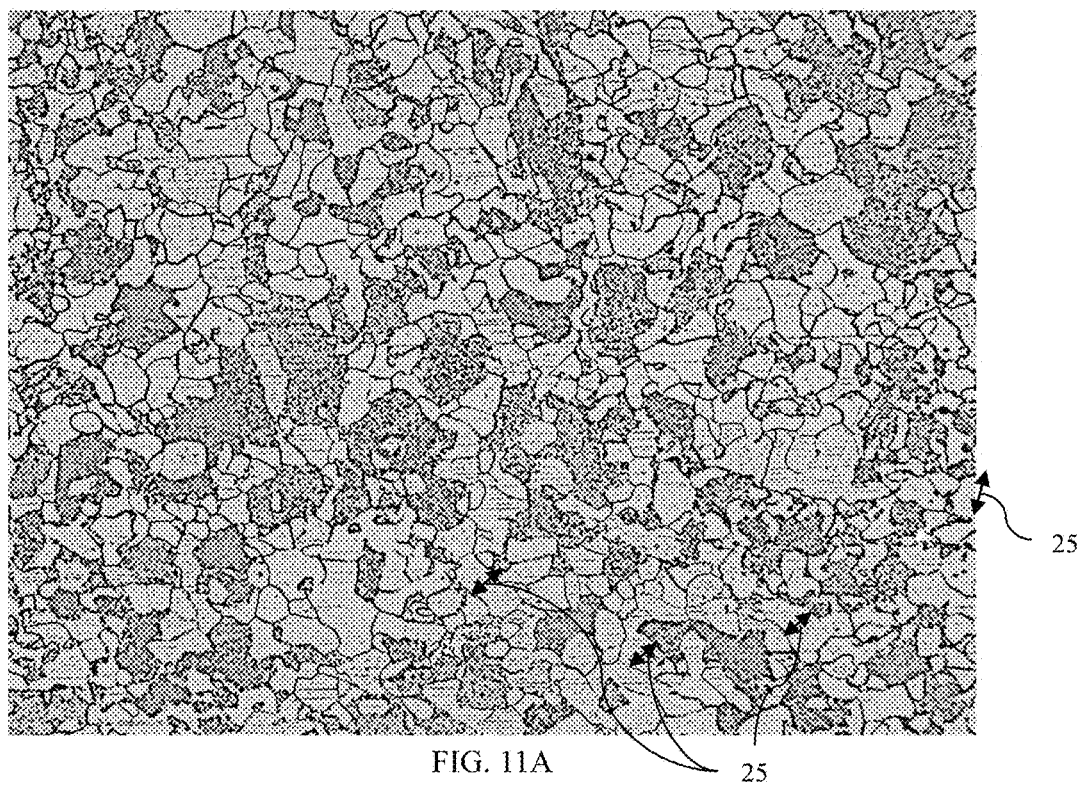
FIGS. 11A-11B are micrographs of microstructural images of formed objects according to the embodiments of the present invention.
Figure 11B:
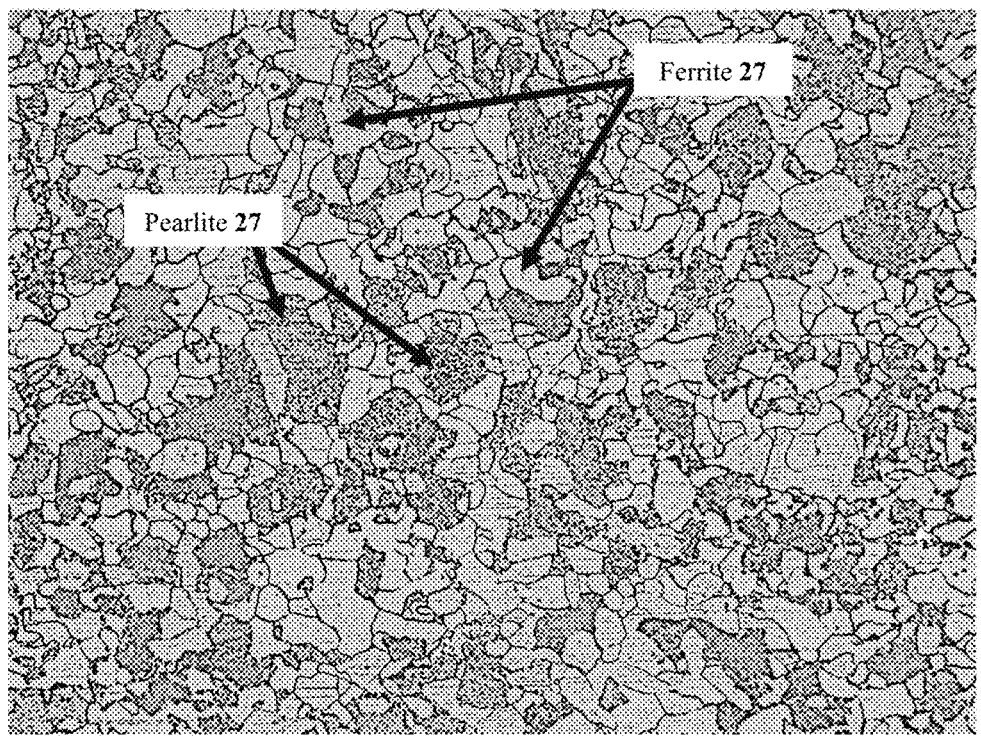

A representative image of a low carbon steel microstructure is shown in FIG. 11A. Darker regions represent areas where the etchant preferentially corroded material revealing ferrite grains and grain boundaries. This image has been analyzed with an image processing software to segment the individual grains, which are shown with black boundaries. The segmented image is used to determine an effective grain size 25 using standard methods like the mean linear intercept. The different microstructure phases 27 are labeled on the same microstructure in FIG. 11B, with darker areas representing pearlite, and lighter regions ferrite. Statistics on the grain geometry, grain size 25, grain orientation, and volume fraction of microstructure phases 27 can be collected from each microstructure image using image processing or manual methods.

Figure 12A:
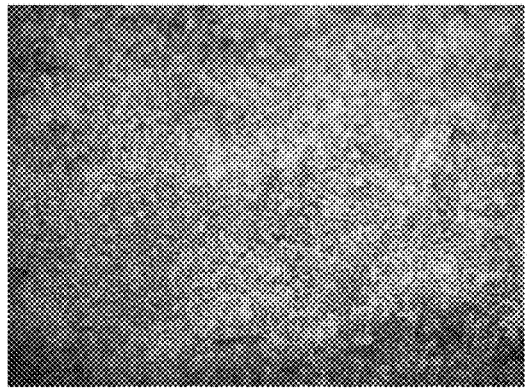
FIGS. 12A-12F are micrographs of microstructural grain images at different locations of a weld on formed objects according to the embodiments of the present invention.
Figure 12D:
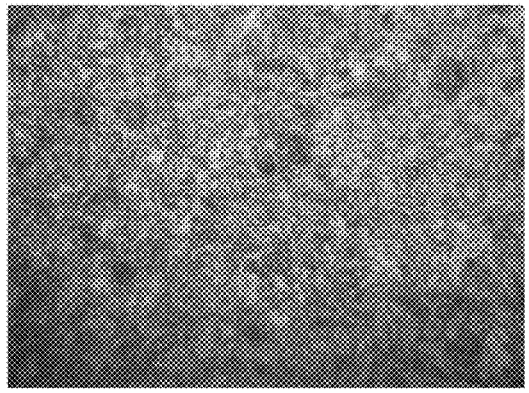
Figure 12B:
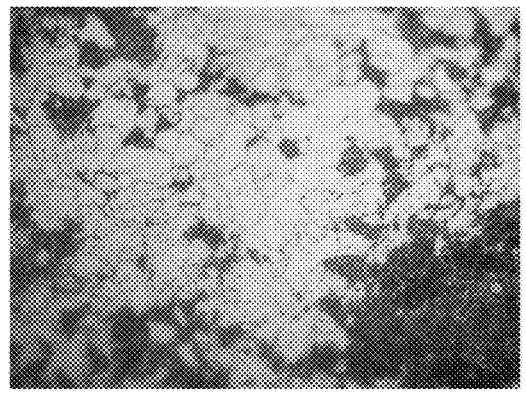
Figure 12E:
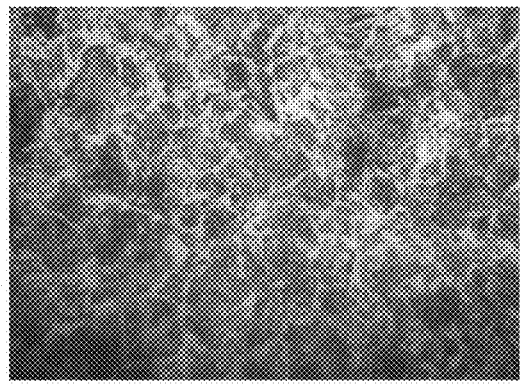
Figure 12C:
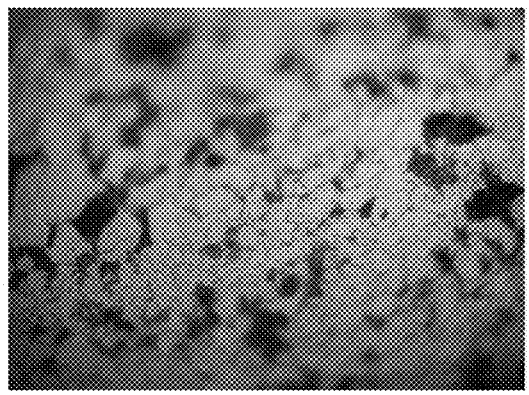
Figure 12F:
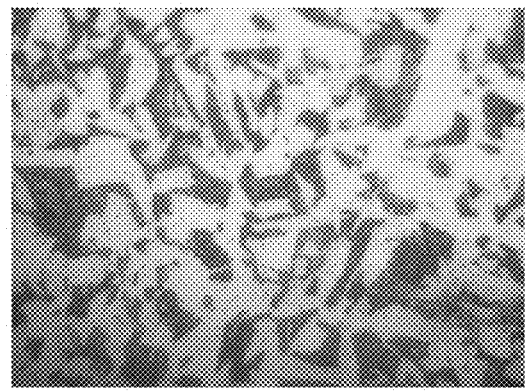

A weld microstructure analysis 28 (referred to in FIGS. 17 and 19A) can be performed by examining and/or quantifying features of the weld 2 microstructure. In one embodiment, multiple metallographic images are collected that allow for observation of relative changes in the microstructure from the base material 3, through the HAZ 6 and near the bondline 4. FIGS. 12A-12F show microscopic images used for weld microstructure analysis 28 of a HF-ERW 53 and LF-ERW 52 weld 2. The HF-ERW 53 weld 2 has a very small grain size 25 near the bondline (FIG. 12A), with a coarsened microstructure and larger grain size 25 in the HAZ 6 (FIG. 12B), that is similar to the grain size 25 in the base material 3 (FIG. 12C). These observations are consistent with the measured hardness profiles for HF-ERW 53 welds 2 that often exhibit a large spike in hardness near the bondline 4. The LF-ERW 52 weld 2 has a very different behavior, with huge changes in grain morphology and grain size 25 near the bondline 4 (FIG. 12D), HAZ 6 (FIG. 12E), and base material 3 (FIG. 12F). The HAZ 6 image (FIG. 12E) also shows a bainitic or Widmanstatten ferrite phase that would indicate an increased risk of brittle behavior. In another embodiment, the weld microstructure analysis identifies a large proportion of hard phase such as Martensite which indicates a susceptibility to brittle behavior and low toughness.

Figure 13:
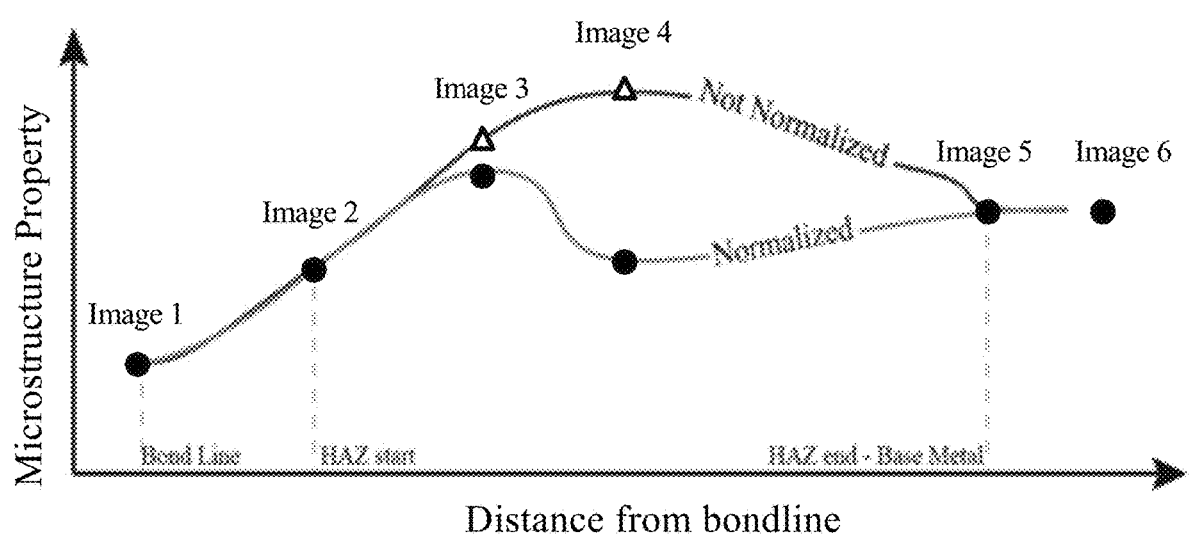
FIG. 13 is a schematic of a weld microstructure profile portraying the changes of microstructure properties from the bondline to the base material of a formed object according to the embodiments of the present invention.

The weld microstructure analysis 28 can also be used to quantify changes in microstructure properties. This is shown schematically in FIG. 13, where a weld microstructure profile is shown with expected differences in microstructure properties at the bond line 4, HAZ 6, and base material 3 of a weld 2 that has been normalized with a PWHT 8, and a weld 2 that has not been normalized. The weld microstructure profile can be constructed by interpolating calculated microstructure properties from image analysis of microstructure images obtained at locations throughout the weld 2. The normalized weld 2 with an effective PWHT 8 would exhibit a reduced change in microstructure properties compared to a weld that 2 was not normalized. In one embodiment, for each weld microstructure profile, the maximum relative change from the base material 3 microstructure property is determined. In another embodiment, the relative change from the base material 3 in the HAZ 6 and bond line 4 are determined. In another embodiment, the relative changes are normalized by the base material 3 microstructure property to determine a relative percent change. Specific embodiments of microstructure properties could include grain size 25, grain morphology, grain texture, and volume fraction of chemical phases. These quantitative and qualitative determinations have important implications on the provided index of weld quality 46.

Specific Embodiments of Determining an Index of Vintage

The index of vintage 24 (referred to in FIGS. 17 and 19A) reflects quality of processing controls and manufacturing technology that was available when the formed object 1 and weld 2 were constructed. Additional factors that are known to vary with vintage is the quality of the steel, control of welding process parameters, effectiveness of PWHT 8, and the base material bulk mechanical properties 70 (referred to in FIG. 19A). An index of vintage 24 also reflects the possible welding processes that could have been used to manufacture the weld 2. For example, lap-welded 49 longitudinal pipes were largely produced between 1920 and 1930. Most LF-ERW 52 and flash-welded 48 pipes were manufactured between 1920 and 1970, after which they were almost completely replaced by HF-ERW 53 welds 2. SAW 50 pipe started in the 1930s and became the standard method for larger-diameter pipe joints by the 1950s.

Figure 14:
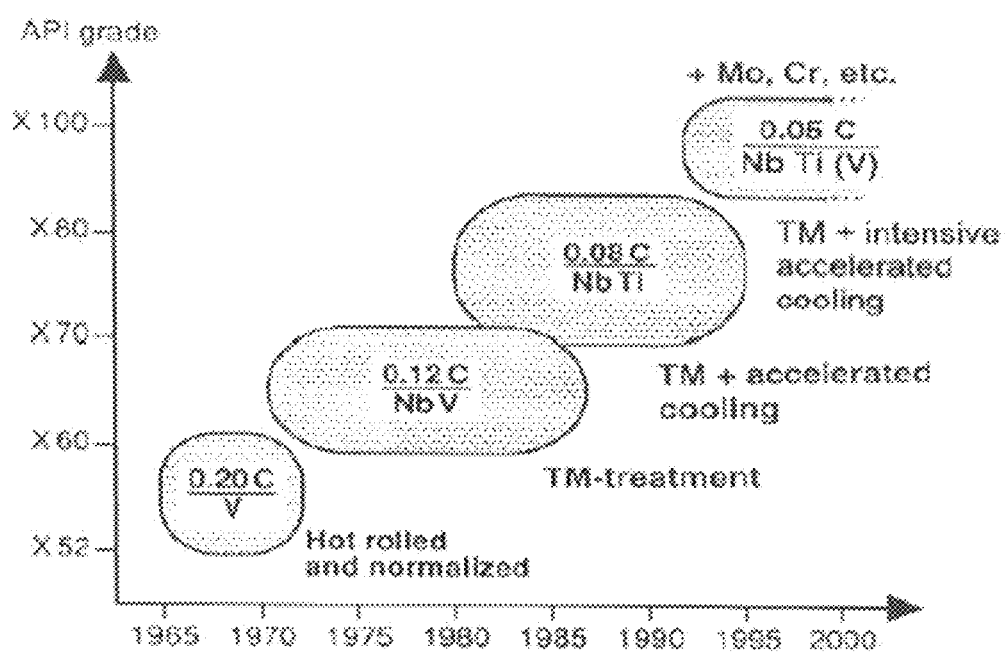
FIG. 14 is a schematic of the chemical composition of the weld of formed objects according to embodiments of the present invention.

The index of vintage 24 can be determined directly from construction records or material test reports (MTR) if they are available. However, for some vintage formed objects 1 these documents are incomplete or have been lost. Indirect methods of determining an index of vintage 24 include examining the material microstructure because modern pipes are known to have a smaller grain size 25 than vintage pipes due to the more recent developments of microalloying, oxygen steel making, continuous casting, and thermomechanical processing to the manufacturing industry. Vintage pipes prior to 1970 may exhibit a higher sulfur content, in the form of manganese sulfide, as a result of the more outdated manufacturing processes, higher variability and reduced quality control. As a result, high sulfur content from the measured chemical composition 22 provide one indication of an older formed objects 1. Another chemical composition 22 consideration is the carbon content of a steel formed object. More recent construction is capable of further reducing the carbon content for higher toughness in pipes manufactured after the 1970s. Therefore, a lower carbon content could be associated with HF-ERW 53 welds 2. Additional trace elements and carbon content trends are shown as a function of formed object 1 material grade and vintage in FIG. 14.

Specific Embodiments of Measuring Weld Defects

Figure 15A:
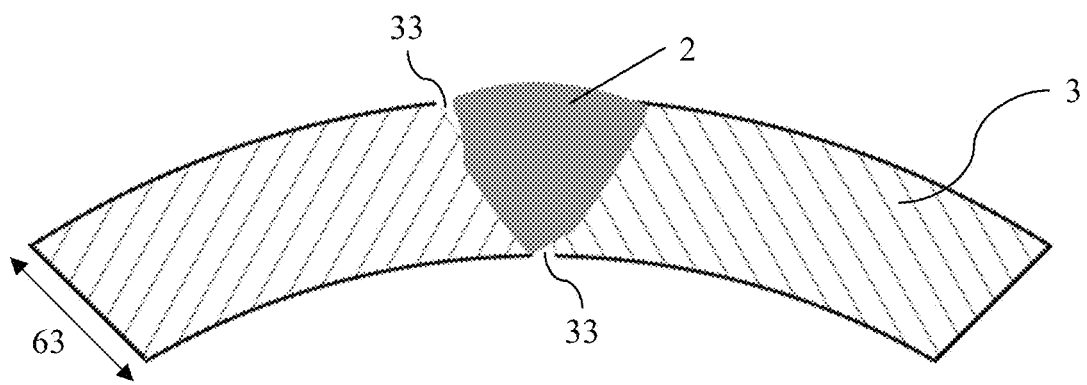
FIGS. 15A-15G are schematics of weld defects at the weld of formed objects according to embodiments of the present invention.
Figure 15B:
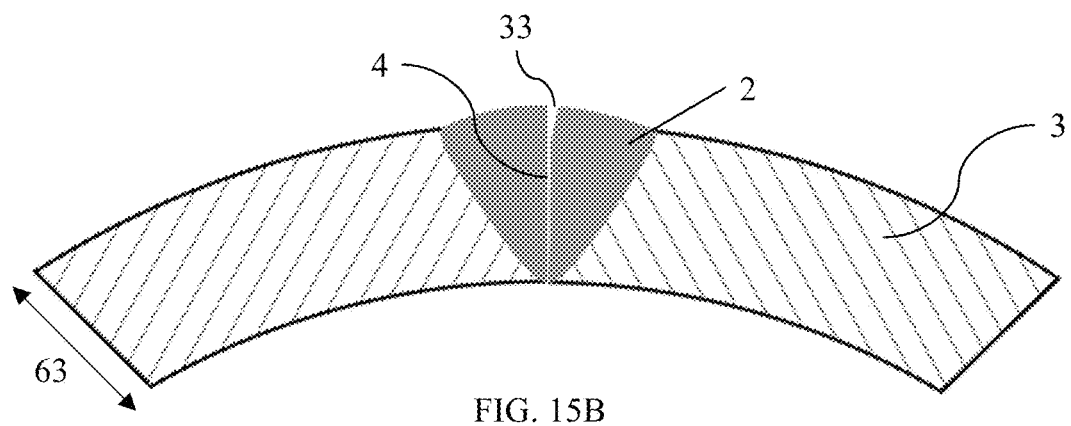
Figure 15C:
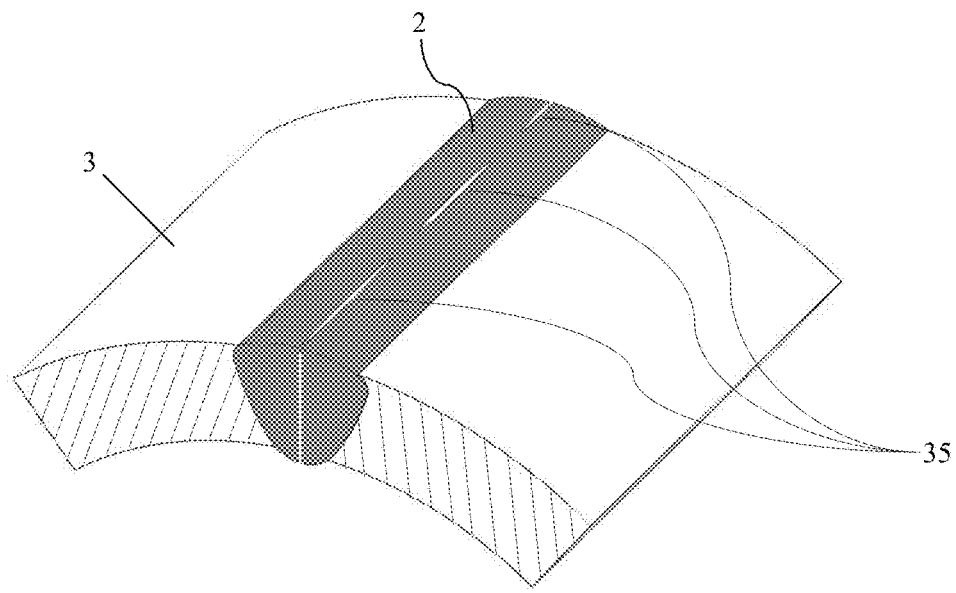
Figure 15D:
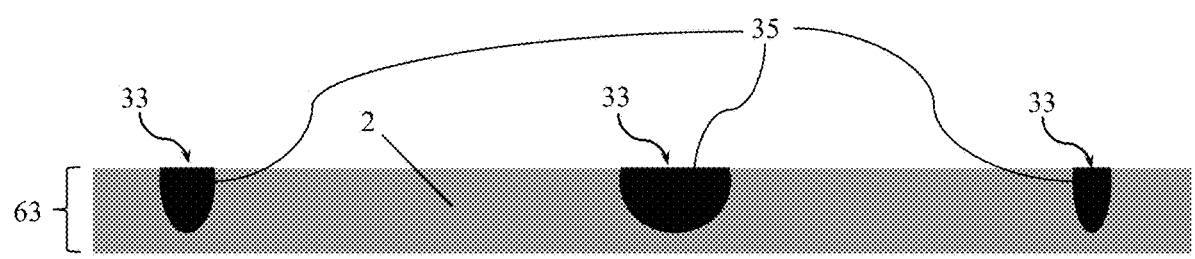
Figure 15E:
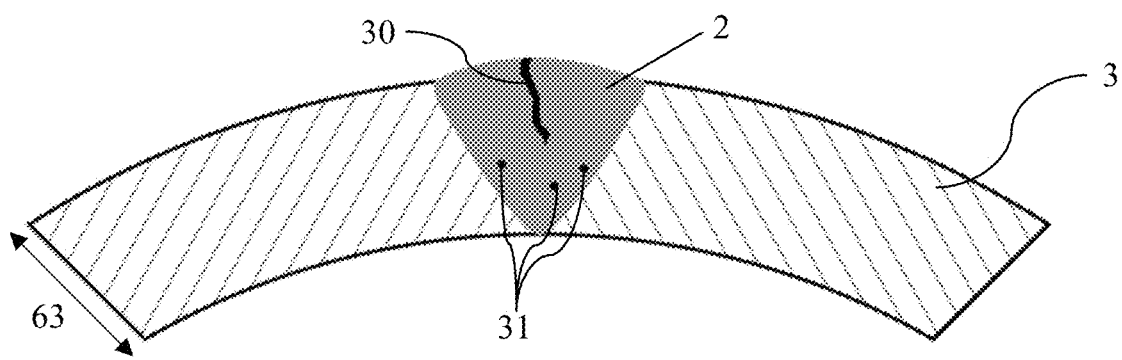
Figure 15F:
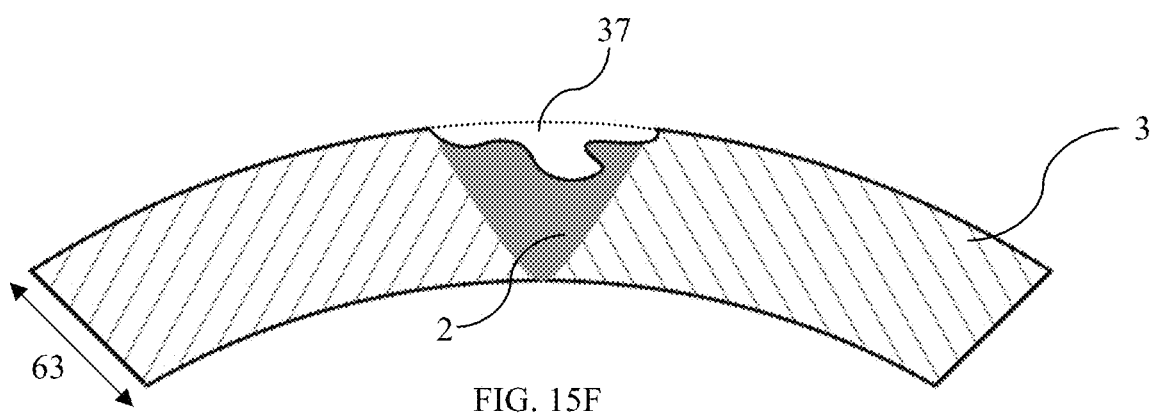
Figure 15G:
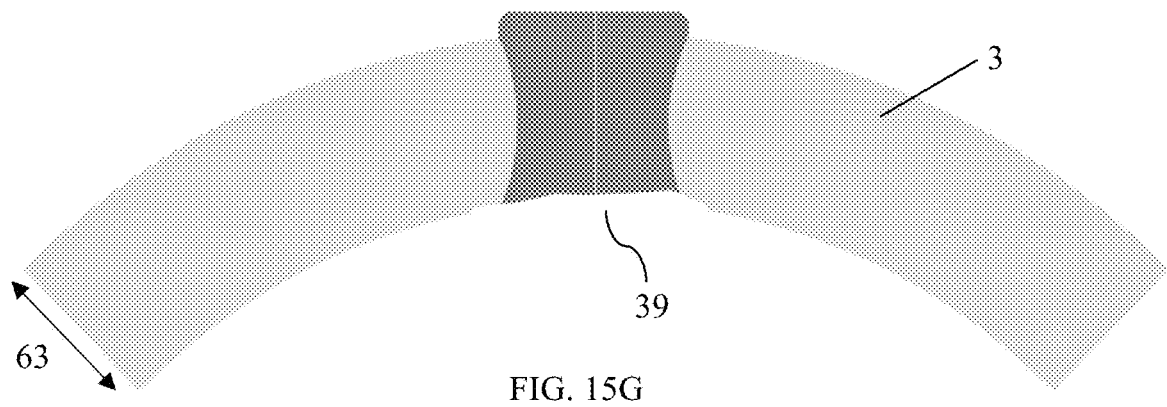

Defects are weak regions in a formed object 1 that reduce the capacity and can grow over time under fluctuations in loads and exposure to corrosive environments. Furthermore, the applied stress required to propagate a crack is dependent on the material fracture toughness and the size of any existing defects or flaws. Thus, weld defects 29 (referred to in FIG. 19A) act as sources of weld 2 failures and through flaw assessment 83 influence the provided index of weld quality 46 by reducing the capacity, remaining life, and effective toughness. Embodiments of potential weld defects 29 are shown in FIGS. 15A-15G. The embodiments in FIG. 15A-15B show a lack of fusion defect 33 where a weld 2 had insufficient heat, pressure and/or intimate contact between opposing surfaces during fabrication, resulting in a region of reduced bonding. The lack of fusion 33 is between the weld 2 and base material 3 in FIG. 15A, and is at the bondline 4 in FIG. 15B. A lack of fusion 33 at the bondline 4 in an ERW 51 weld 2 is often referred to as a cold weld. FIGS. 15C-15D show embodiments of a stitching defect 35, where the weld 2 exhibits intermittent regions that have a lack of fusion defect 33 along the length of the weld 2. FIG. 15E is an embodiment of cracks 30 which are sharp geometrical features that may be internal or external to the weld 2 and/or base material 3, and pores 31 which are voids surrounded by solid material that may have rounded or sharp features. The embodiment in FIG. 15F is selective weld seam corrosion 37 where chemical and geometrical factors lead to preferential corrosion in the weld 2, resulting in a loss in wall thickness 63. Another embodiment is a weld trim defect 39 which is shown in FIG. 15G as the removal of excess flash during manufacturing that causes localized regions of reduced wall thickness 63 in the weld 2 and base material 3. Additional embodiments that are not shown are inclusion defects where contaminants during manufacturing that differ from the base material 3 and/or weld 2 material result in reduced bonding in the weld 2 and stress corrosion cracking which is when cracks and/or pores grow over time due to the combined effects of external loading and a corrosive environment.

These weld defects 29 can be located and sized through defect measurement devices. These include an ultrasonic testing gauge which uses ultrasound waves to identify the size and location of defects as well as measure the wall thickness 63 of the formed object 1 and weld 2, magnetic particle inspection which uses the application of magnetic particles and a magnetic field to identify sub-surface defects such as cracks 30, pores 31, and lack of fusion 33, a magnetic flux leakage instrument which applies a magnetic field to steel formed objects 1 to identify damaged regions and estimate the depth of wall thickness 63 loss, computed tomography devices which use X-rays to penetrate a formed object 1 to visualize and size weld defects 29, and pipeline inspection gauges which are in-line inspection instruments for pipeline formed objects 1 that travel inside the pipeline to measure weld defects 29 using one or more of these defect measurement devices. The weld defects 29 that are measured with defect measurement devices can be analyzed to determine the type of defect, size, frequency, and geometry in the weld 2.

Specific Embodiments of Measuring Base material Bulk Mechanical Properties

The quality of the weld 2 is dependent on the quality of the base material 3 that the weld 2 is joining. The base material 3 controls the weldability, compatibility with any filler weld material 64, concentration of unwanted inclusions and contaminants transferred to the weld 2 during melting, and the composition of the weld 2 if no filler weld material 64 is used such as in an ERW 51 weld 2. It is generally accepted that the quality of the weld 2 cannot exceed the quality of the base material 3 in the absence of defects or flaws. Therefore, an index of weld quality 46 may be some proportion of the base material bulk mechanical properties 70. Bulk indicates that the measurement considers the geometry and wall thickness 63 of the formed object 1 and measures a much greater volume than a surface mechanical property measured with a contact mechanics test 13.

Base material bulk mechanical properties 70 (referred to in FIG. 19A) can be measured with traditional standardized methods. Embodiments of base material bulk mechanical properties 70 from destructive tests include fracture toughness evaluation based on the measured stress intensity factor (K), J-integral (J), and/or crack-tip-opening-displacement (CTOD), Charpy V-Notch (CVN) or Izod impact testing to measure the absorbed energy, tensile testing of coupons to evaluate strength and ductility, and fatigue testing to evaluate the resistance to the growth of a crack under cyclic loading. Nondestructive techniques can also be applied to measure base material bulk mechanical properties 70 in-situ. These embodiments include the Hardness, Strength, and Ductility (HSD) Tester which uses frictional sliding 59 tests to predict tensile stress-strain behavior, the Nondestructive Toughness Tester (NDTT) which uses frictional sliding 59 tests to predict fracture toughness properties, and instrumented indentation testing (IIT) which uses a repeated indentation 60 tests of increasing force to predict both tensile stress-strain behavior and fracture toughness. In another embodiment, the base material bulk mechanical properties 70 are determined by reference to material test reports that provide the destructive test results when the formed object 1 was initially manufactured.

Specific Embodiments of a Weld Database

Figure 16:
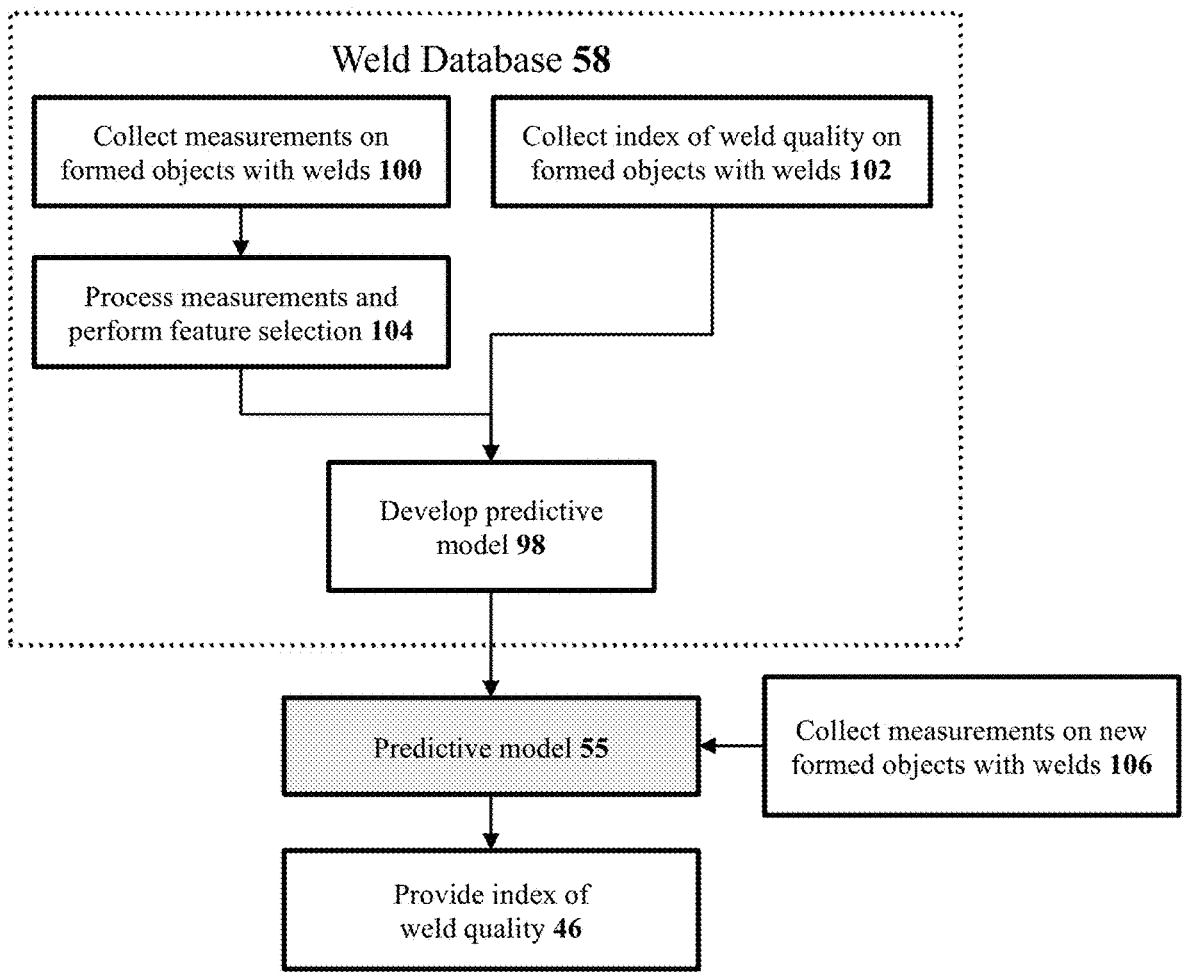
FIG. 16 is a schematic of the methodology for developing a predictive model using a weld database according to embodiments of the present invention.

An embodiment that implements a weld database 58 is shown in FIG. 16. The weld database is developed by collecting measurements on formed objects with welds 100. These measurements are collected using the same methods and procedures to ensure consistency and allow for comparisons. Embodiments of these measurements include the base material surface mechanical property 78, weld surface mechanical property 76, and measured weld width 96 (referred to in FIG. 2), and chemical composition 22, weld microstructure analysis 28, index of vintage 24, weld defects 29, and base material bulk mechanical property 70 (referred to in FIGS. 17 and 19A). These measurements are processed to perform feature selection 104. Embodiments of these features include the relative difference in the base material surface mechanical property 78 and weld surface mechanical property 76, etched weld width 20, weld microstructure profile, carbon equivalent, base material bulk yield strength, year of installation, and other parameters that have been discussed throughout this specification. After processing measurements to perform feature extraction 104, the extracted features are used to develop a predictive model 98 that establishes relationships with a collected index of weld quality on formed objects with welds 102 that is measured on the same samples that the other measurements were collected 100. The form of the relationships between the extracted features and collected index of weld quality 102 depends on the assumptions and degrees of freedom of the selected predictive model 55 algorithm. One embodiment of a predictive model 55 is a classification model 56 that considers one or more extracted features to determine one or more categories of an index of weld quality 46. An embodiment of a classification model 56 category is the determination of the welding process as LF-ERW 52, HF-ERW 53, or HFN-ERW 54, referred to in FIG. 17. Another embodiment of a predictive model 55 is a regression model 57 (referred to in FIG. 19A) that determines a quantitative index of weld quality 46. Embodiments of a regression model 57 index of weld quality 46 is the weld toughness or maximum weld allowable flaw size. Embodiments of predictive model 55 algorithms include multiple linear regression, nonlinear regression, regression trees, neural networks, deep learning, Bayesian regression, Bayesian classification, classification trees, support vector machines, and other tools of machine learning. The performance of the predicted model 55 can be validated by using established data science techniques to assess model sensitivity, accuracy, uncertainty, confidence intervals, and statistical significance. For all predictive models 55, care must be taken to avoid overfitting or biasing the model as more measurements and parameters are included.

After developing a predictive model 98, the predictive model 55 can be used to provide an index of weld quality 46 based on the collection of measurements on new formed objects with welds 106 that are not part of the weld database 58. The measurements are collected using the same procedures and methods for data collection and feature extraction that were used for weld database 58 samples. New formed objects 1 with welds 2 should have properties and characteristics that are similar to the samples that already exist in the weld database 58. The weld database 58 can increase in size by including additional formed objects 1 with welds 2 that have known indices of weld quality 46. A larger weld database 58 results in more robust and accurate predictive models 55 because the weld database 58 becomes more representative of other formed objects 1 with a weld 2.

Specific Embodiments of Evaluating a Welding Process

The welding process is an indirect measurement of an index of weld quality 46, but some industry practitioners have used the welding process to assign quantitative metrics based on differences in expected performance for the different welding processes. A general embodiment for the evaluation of a welding process is shown in FIG. 17. Visual inspection of the weld 84 is used to classify the welding process as flash-welded 48, SAW 50, or lap-welded 49. However, additional measurements and processing parameters are required for ERW 51 welds 2 with no distinguishing weld reinforcement 9 or surface characteristic 87. Multiple measurements can be considered to evaluate the welding process, including the weld width 19, features from a weld microstructure analysis 28, relative difference in surface mechanical properties 80 from contact mechanics tests 13 in the weld 2 and base material 3, index of vintage 24, and chemical composition 22. In one embodiment, only the ERW 51 weld width 19 and the relative differences in surface mechanical properties from contact mechanics tests 13 are included in the classification model 56. In another embodiment, one or more of the remaining measurements shown in FIG. 17 are included to provide a more accurate and reliable prediction of the welding process.

Figure 18A:
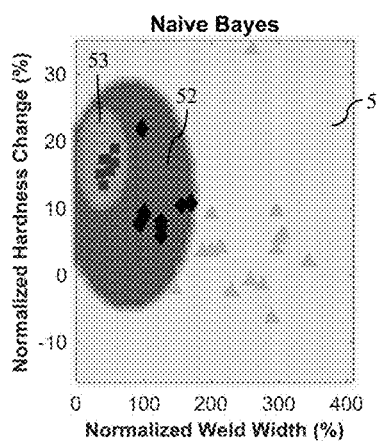
FIGS. 18A-18C are schematics of different classification models for ERW welds.
Figure 18B:
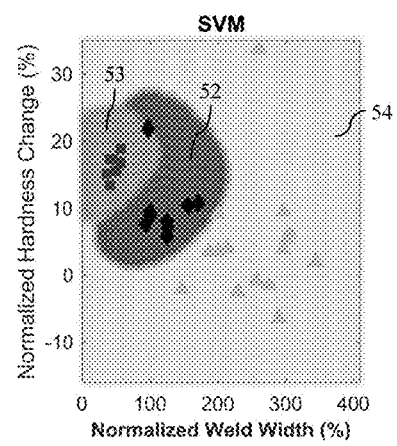
Figure 18C:
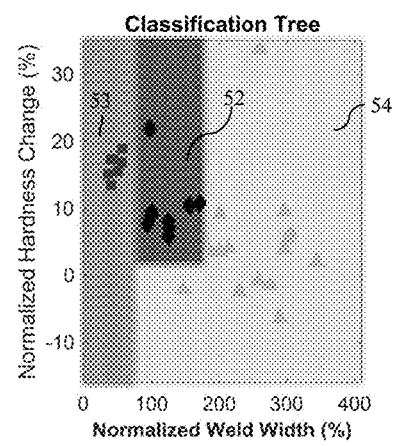

An embodiment of different classification models 56 for a weld database 58 with thirty-three formed objects 1 with ERW 51 welds 2 and considering the measured normalized average relative hardness differences from frictional sliding tests 59 and the normalized etched weld width 74 are shown in FIGS. 18A-18C. Each figure shows a different classification model 56, but the same formed objects 1 with known ERW 51 welding processes. The decision boundaries between different welding processes can be identified by the different shaded regions on the plots. For this application, the naïve Bayes (FIG. 18A) and classification tree (FIG. 18C) models perform the best because they correctly classify every ERW 51 welding process, whereas the support vector machine (FIG. 18B) has one incorrect weld 2. However, if carbon content is considered by the support vector machine classification model 56, then all the welding processes are correctly classified, illustrating that predictive model 55 performance can improve as more parameters are considered. Another feature of many predictive models 55 is the ability to determine uncertainty in a prediction. With the naïve Bayes model, samples that are closer to the decision boundary have a reduced probability of being part of their classified welding process. This probability and uncertainty can be considered in many risk and fitness for service assessments.

Specific Embodiments of Evaluating a Weld Toughness and Maximum Weld Allowable Flaw Size A direct index of weld quality 46 that is used in fitness for service and engineering critical assessment include the weld toughness and maximum weld allowable flaw size. A general embodiment for a regression model 57 for these indices of weld quality 46 is shown in FIG. 19A. In this embodiment, the predictive model 55 starts with a classified welding process, but in other embodiments the welding process may be unknown. The regression model 57 considers multiple parameters that are measured on the formed object 1 and weld 2, including the weld width 19, features from a weld microstructure analysis 28, relative difference in surface mechanical properties 80 from contact mechanics tests 13 in the weld 2 and base material 3, index of vintage 24, chemical composition 22, base material bulk mechanical properties 70, and flaw assessment 83 of weld defects 29. In one embodiment, the direct index of weld quality 46 is determined as a proportion of the base material bulk mechanical properties 70 for the same quantitative index (e.g. the weld toughness is 85% of the base material toughness). In another embodiment, the direct index of weld quality 46 is reduced based on a flaw assessment 83 that would reduce the effective weld toughness.

Figure 19B:
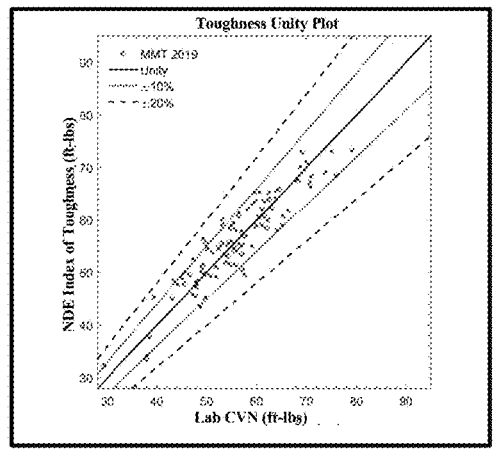

An embodiment of a regression model 57 used to predict weld toughness is shown in FIG. 19B. This is a unity plot that directly compares the predictive model 55 with the traditional laboratory measurement of the index of weld quality 46. The unity plot demonstrates correlation between the model predictions and actual measurements and can be used to assess model performance and uncertainty.

The embodiments of the invention described above are intended to be merely exemplary; numerous variations and modifications will be apparent to those skilled in the art. All such variations and modifications are intended to be within the scope of the present invention as defined by the appended claims.

What is claimed is:

1. A method of evaluating a weld in a formed object having an exterior surface, the method comprising:
   a. performing, on the exterior surface of the formed object, a contact mechanics test of a first region that includes the weld and storing one or more corresponding weld surface mechanical property measurements;
   b. performing, on the exterior surface of the formed object, a contact mechanics test of a second region that excludes the weld and storing one or more corresponding base material surface mechanical property measurements;
   c. determining a difference in the weld surface mechanical property measurements and the base material surface mechanical property measurements based on the contact mechanics test in step a and the contact mechanics test in step b;
   d. performing one or more weld width measurements on the exterior surface of the formed object to determine one or more weld widths;
   e. providing one or more wall thickness measurements of the formed object in the first region and the second region to determine one or more wall thicknesses; and
   f. evaluating the weld based on the determined difference in the weld surface mechanical property measurements and the base material surface mechanical property measurements in relation to the determined one or more weld widths and the one or more wall thicknesses of the formed object to provide an index of weld quality.

2. The method of claim 1, wherein performing the contact mechanics test of the first region and performing the contact mechanics test of the second region are performed using a single frictional sliding test.

3. The method of claim 1, wherein performing the contact mechanics test of the first region and/or performing the contact mechanics test of the second region are performed with a grid or linear array of indentations.

4. The method of claim 1, wherein determining the difference in the weld surface mechanical property measurements and the base material surface mechanical property measurements includes comparing an average of the weld surface mechanical property measurements and an average of the base material surface mechanical property measurements.

5. The method of claim 1, wherein determining the difference in the weld surface mechanical property measurements and the base material surface mechanical property measurements includes examining local maxima and minima in the weld surface mechanical property measurements with respect to the base material surface mechanical property measurements.

6. The method of claim 1, wherein performing the one or more weld width measurements includes applying an etchant to the exterior surface of the weld to determine an etched weld width based on size of discolored material within the weld.

7. The method of claim 1, wherein performing the contact mechanics test of the first region includes determining a first region weld surface mechanical property profile and/or performing the contact mechanics test of the second region includes determining a second region weld surface mechanical property profile, wherein performing the one or more weld width measurements includes analyzing relative changes in the first region weld surface mechanical property profile and/or in the second region weld surface mechanical property profile to determine the one or more weld widths.

8. The method of claim 1, wherein the index of weld quality includes a weld toughness.

9. The method of claim 1, wherein the index of weld quality includes a maximum weld allowable flaw size.

10. The method of claim 1, wherein the index of weld quality includes classification of a welding process.

11. The method of claim 1, wherein the evaluating step includes using one or more weld surface mechanical property measurements, base material surface mechanical property measurements, weld width measurements and/or wall thickness measurements stored in a weld database.

12. The method of claim 11, further comprising providing, to the database, the index of weld quality and parameters used in evaluating the index of weld quality.

13. The method of claim 11, wherein the evaluating step further includes determining a confidence interval of the index.

14. The method according to claim 1, further comprising performing a chemical analysis to determine chemical composition of the formed object and/or the weld, wherein the index of weld quality is further based on the chemical composition.

15. The method according to claim 14, wherein determining the chemical composition includes determining the carbon equivalent.

16. The method according to claim 1, further comprising performing a weld microstructural analysis, wherein the index of weld quality is further based on the weld microstructural analysis.

17. The method according to claim 1, further comprising determining an index of age of the formed object, wherein the index of weld quality is further based on the index of age.

18. The method according to claim 1, further comprising determining a weld defect, wherein the index of weld quality is further based on the weld defect.

19. The method according to claim 1, further comprising determining a base material bulk mechanical property, wherein the index of weld quality is further based on the base material bulk mechanical property.

20. The method according to claim 1, further comprising:
   a. performing a chemical analysis to determine chemical composition of the formed object;
   b. performing a chemical analysis to determine chemical composition of the weld;
   c. performing a weld microstructural analysis;
   d. determining an index of age of the formed object;
   e. determining a weld defect; and/or
   f. determining a base material bulk mechanical property, wherein the index of weld quality is based on two or more of the chemical composition of the formed object, the chemical composition of the weld, the weld microstructural analysis, the index of age, the weld defect and/or the base material bulk mechanical property.

\* \* \* \* \*